US006741881B2

(12) United States Patent
Prince

(10) Patent No.: US 6,741,881 B2
(45) Date of Patent: *May 25, 2004

(54) METHOD AND APPARATUS FOR MAGNETIC RESONANCE IMAGING OF ARTERIES USING A MAGNETIC RESONANCE CONTRAST AGENT

(76) Inventor: Martin R. Prince, 2745 Windwood Dr., Apt. 240, Ann Arbor, MI (US) 48105

( * ) Notice: Subject to any disclaimer, the term of this patent is extended or adjusted under 35 U.S.C. 154(b) by 0 days.

This patent is subject to a terminal disclaimer.

(21) Appl. No.: 10/212,527

(22) Filed: Aug. 5, 2002

(65) Prior Publication Data

US 2003/0047083 A1 Mar. 13, 2003

Related U.S. Application Data

(63) Continuation of application No. 09/828,429, filed on Apr. 7, 2001, now Pat. No. 6,463,318, which is a continuation of application No. 09/124,263, filed on Jul. 29, 1998, now Pat. No. 6,240,311, which is a continuation of application No. 08/777,347, filed on Dec. 27, 1996, now Pat. No. 5,792,056, which is a continuation of application No. 08/580,195, filed on Dec. 28, 1995, now Pat. No. 5,590,654, which is a continuation-in-part of application No. 08/420,815, filed on Apr. 12, 1995, now Pat. No. 5,579,767, which is a continuation-in-part of application No. 08/378,384, filed on Jan. 25, 1995, now Pat. No. 5,553,619, which is a continuation-in-part of application No. 08/071,970, filed on Jun. 7, 1993, now Pat. No. 5,417,213.

(51) Int. Cl.[7] .............................................. A61B 5/055
(52) U.S. Cl. ...................... 600/420; 324/307; 324/309
(58) Field of Search ................................ 600/410, 419, 600/420; 324/306, 307, 309

(56) References Cited

U.S. PATENT DOCUMENTS 3,973,554 A    8/1976    Tipton
4,006,736 A    2/1977    Kranys et al.
4,202,333 A    5/1980    Thill et al.

(List continued on next page.)

FOREIGN PATENT DOCUMENTS

EP             543468          5/1993
WO       WO 94/28781     12/1994

OTHER PUBLICATIONS

Bolus–Enhanced Fast—3D—TOF MR Angiography of Peripheral Vascular Occlusive Disease, Thurnher et al., Proceedings of the ISMRM, Apr. 27–May 3, 1996, vol. 2, p. 733.

(List continued on next page.)

Primary Examiner—Ruth S. Smith
(74) Attorney, Agent, or Firm—Neil Steinberg

(57) ABSTRACT

The present invention is a technique and apparatus for providing preferential enhancement of an artery of interest relative to adjacent veins and background tissue by correlating the collection of a predetermined portion of data of a magnetic resonance contrast image during the arterial phase of the magnetic resonance contrast enhancement. The arterial phase of the contrast enhancement may be described as a period of a maximum, substantially elevated, or elevated contrast concentration in the artery of interest relative to adjacent veins. The present invention includes a detection system for monitoring and detecting the arrival of the contrast agent in the artery and tissues of interest. When the concentration of contrast agent in the artery of the region of interest is maximum, substantially elevated or elevated (e.g., about 20–50% greater than the response of the region of interest to a series of magnetic resonance pulses before administration of a magnetic resonance contrast agent), a predetermined portion of the magnetic resonance image data (e.g., data which is representative of the center of k-space) may be acquired. Thus, the present invention facilitates synchronization between collecting the central portion of k-space image data with the arterial phase of contrast enhancement. The center of k-space corresponds to the lowest spatial frequency data which dominates image contrast.

20 Claims, 11 Drawing Sheets

U.S. PATENT DOCUMENTS

| | | | |
|---|---|---|---|
| 4,298,000 A | 11/1981 | Thill et al. |
| 4,430,079 A | 2/1984 | Thill et al. |
| 4,585,008 A | 4/1986 | Jarkewicz |
| 4,585,941 A | 4/1986 | Bergner |
| 4,597,754 A | 7/1986 | Thill et al. |
| 4,718,424 A | 1/1988 | Nishimura |
| 4,770,183 A | 9/1988 | Groman et al. |
| 4,777,957 A | 10/1988 | Wehrli et al. |
| 4,822,594 A | 4/1989 | Gibby |
| 4,826,673 A | 5/1989 | Dean et al. |
| 4,865,043 A | 9/1989 | Shimoni |
| 4,877,599 A | 10/1989 | Lees |
| 4,880,008 A | 11/1989 | Lauffer |
| 4,915,111 A | 4/1990 | Sano et al. |
| 5,010,191 A | 4/1991 | Engelstad et al. |
| 5,011,686 A | 4/1991 | Pang |
| 5,034,694 A | 7/1991 | Sattin et al. |
| 5,055,288 A | 10/1991 | Lewis et al. |
| 5,078,986 A | 1/1992 | Bosworth et al. |
| 5,087,439 A | 2/1992 | Quay |
| 5,111,492 A | 5/1992 | Klausz |
| 5,141,740 A | 8/1992 | Rajagopalan et al. |
| 5,167,232 A | 12/1992 | Parker et al. |
| 5,190,744 A | 3/1993 | Rocklage et al. |
| 5,204,629 A | 4/1993 | Ueyama |
| 5,260,050 A | 11/1993 | Ranney |
| 5,287,273 A | 2/1994 | Kupfer et al. |
| 5,301,672 A | 4/1994 | Kalender |
| 5,305,751 A | 4/1994 | Chopp et al. |
| 5,315,997 A | 5/1994 | Widder et al. |
| 5,341,099 A | 8/1994 | Suzuki |
| 5,398,686 A | 3/1995 | Inoue et al. |
| 5,417,213 A | 5/1995 | Prince |
| 5,423,315 A | 6/1995 | Margosian et al. |
| 5,494,036 A | 2/1996 | Uber, III et al. |
| 5,515,863 A | 5/1996 | Damadian |
| 5,522,390 A | 6/1996 | Tuithof et al. |
| 5,553,619 A | 9/1996 | Prince |
| 5,579,767 A | 12/1996 | Prince |
| 5,590,654 A | 1/1997 | Prince |
| 5,684,398 A | 11/1997 | Takiguchi et al. |
| 5,746,208 A | 5/1998 | Prince |
| 5,762,065 A | 6/1998 | Prince |
| 5,792,056 A | 8/1998 | Prince |
| 5,799,649 A | 9/1998 | Prince |
| 6,230,041 B1 | 5/2001 | Prince |
| 6,240,311 B1 | 5/2001 | Prince |
| 6,243,600 B1 | 6/2001 | Prince |
| 6,278,892 B1 | 8/2001 | Prince |

OTHER PUBLICATIONS

"Clinical application of pulmonary 3 dimensional time-of-flight MR angiography with breath-holding using a contrast medium", Isoda, et al., Society of Magnetic Resonance in Medicine, 11 th Annual Scientific Meeting, Aug. 8–14, 1992, Berlin, Germany, Works in Progress, p. 3119, XP002111479.

"Fast-scan magnetic resonance: Principles and applications", Wehrli, Magnetic Resonance Quarterly, v. 6, No. 3, 1990, p. 165–236, XP002111477.

A Rapid Interleaved Method for Measuring Signal Intensity Curves in both Blood and Tissue during Contrast Agent Administration, Taylor et al., Magnetic Resonance in Medicine, 30, 1993, pp. 744–749.

"Cerebrovascular Magnetic Resonance Angiography", Wesbey et al., J. Vascular Surgery 1992, vol. 16, No. 4, pp. 619–632.

"Volume MR Angiography: Methods to Achieve Very Short Echo Times", Schmalbrock et al., Radiology 1990, vol. 175, pp. 861–865.

"Three Dimension (Volume) Gradient–Echo Imaging of the Carotid Bifurcation: Preliminary Clinical Experience", Masaryk et al., Radiology 1989, vol. 171, pp. 801–806.

"Gadolinium–enhanced Magnitude Contrast MR Angiography of Popliteal and Tibial Arteries", Lossef et al., Radiology 1989, vol. 184, pp. 349–355.

"Intercranial Circulation: Preliminary Clinical Results with Three–Dimensional (Volume) MR Angiography", Masaryk et al., Radiology 1989, vol. 171, pp. 793–799.

"Abdominal Aorta and Renal Artery Stenosis: Evaluation with MR Angiography", Kim, et al.,Radiology, vol. 174, pp. 727–731, Mar. 1990.

"Intercranial Vascular Lesions: Optimization and Clinical Evaluation of Three–Dimensional Time–of–Flight MR Angiography", Marchal, et al., Radiology, vol. 175, pp. 443–448, May 1990.

"Normal Venous Anatomy of the Brain: Demonstration with Gadopentatate Dimeglumine in Enhanced 3–D MR Angiography", Chakeres, et al., AJR, vol. 156, pp. 161–172, Jan. 1991.

"Three–dimensional time–of–Flight MR Angiography: Applications in the Abdomen and Thorax", Lewin, et al., Radiology, vol. 179, No. 1, pp. 261–264, Apr. 1991.

"Safety of Gadolinium–DPTA: Extended Clinical Experience", Niendorf, et al., SMRM Workshop on Contrast Enhanced Magnetic Resonance, May 23–25, 1991.

"Fast Time–of–Flight MR Angiography with Improved Background Suppression", Edelman, et al, Radiology, vol. 179, pp. 867–870, Jun. 1991.

"Assessment of Carotid Artery Stenosis by MR Angiography: Comparison with X–ray Angiography and Color Coded Doppler Ultrasound", Anderson, et al., AJNR, vol. 13, pp. 989–1003, May/Jun. 1992.

"Gadolinium–enhanced High–Resolution MR Angiography with Adaptive Vessel Tracking: Preliminary Result in the Intercranial Circulation", Lin, et al, JMRI, vol. 2, pp. 277–284, May/Jun. 1992.

"Experience with High–Dose Gadolinium MR Imaging in the Evaluation of Brain Metastases", Yuh, et al., AJNR, vol. 13, pp. 335–345, Jan./Feb. 1992.

"Frequency Dependence of Tissue Relaxation Times", Bottomley, Relaxation Relaxometry, 1987, pp. 1075–1086.

"Abdominal Aortography with Dynamic High–Dose Gadopentetate Dimeglumine", Prince, SMRM 12th Annual Meeting, Aug., 1993.

"Dynamic Gadolinium–Enhanced Three–dimensional Abdominal MR Arteriography", Prince et al.,JMRI, vol. 3, No. 6 Nov./Dec. 1993, pp. 877–881.

"Gadolinium–enhanced MR Aortography", Prince, Radiology, vol. 191, No. 1,pp. 155–164, Apr. 1994.

"Optimizing Blood Vessel Contrast in Fast Three–Dimensional MRI", Haacke, et al., SMRM Workshop on MR Imaging of Blood Flow, Mar. 13–14, 1989.

"Magnetic Resonance Angiography of the Thoracic Aorta", Prince, et al., Magnetic Resonance Angiography: A Practical Approach, McGraw–Hill, Incorporated, 1995, Chapter 10, pp. 131–138.

"Contrast Enhancement in Abdominal CT: Bolus vs. Infusion", Burgener, et al., AJR, vol. 137, pp. 351–358, 1981.

"MRA Adds Value in Body Imaging",Prince, MR, vol. 5, No. 3, pp. 29–31, Summer 1995.

"3D–MR–Angiographie mit Gd–DTPA", Seiderer, et al., Fortschr. Rontgenstr., 152–153 (1990), pp. 327–332.

"Fast Magnetic Resonance Angiography Using Turbo–FLASH Sequences in Advanced Aortoiliac Disease", Sivananthan, et al., The British Journal of Radiology, vol. 66, No. 792, pp. 1103–1110, Dec. 1993.

"Contrast–Enhanced Magnetic Resonance Tomoangiography: A New Imaging Technique for Studying Thoracic Great Vessels", Revel, et al., Magnetic Resonance Imaging, vol. 11, pp. 1101–1105, Nov. 8, 1993.

"MR Imaging (Including MR Angiography) of Abdominal Aortic Aneurysms: Comparison with Conventional Angiography", Kaufman, et al., AJR, 163, pp. 203–210, Jul. 1994.

"Gadolinium–Enhanced MR Aortography", Prince, Radiology, p. 193, Nov. 1994.

"Magnetic Resonance Angiography of the Renal and Visceral Arteries", Kaufman, et al., Magnetic Resonance Angiography: A Practical Approach, McGraw–Hill, Incorporated, 1995, Chapter 12, pp. 161–170.

"Gadolinium–Enhanced Magnetic Resonance Angiography of Abdominal Aortic Aneurysms", Prince, et al., Journal of Vascular Surgery, vol. 21, No. 4, pp. 656–669, Apr. 1995.

"Breath–Hold Gadolinium–Enhanced MR Angiography of the Abdominal Aorta and its Major Branches", Prince, et al., Radiology, vol. 197, No. 3, pp. 785–792, Dec. 1995.

"Gadolinium Enhanced MR Imaging of Vascular Stents", Matsumoto et al., Journal of Computer Assisted Tomography, vol. 14, No. 3, pp. 357–361, May/Jun. 1990.

Magnetic Resonance Angiography, Concepts & Applications, Potchen et al., chapter 16, Magnetopharmaceuticals as contrasts agents, Marchal et al., pp. 305–322, 1993.

"Evaluation of Renal Artery Stenosis with Dynamic Gadolinium–Enhanced MR Angiogrpahy: Work in Progress", Rieumont, et al., Radiology, p. 193, Nov. 1994.

"Fast Three–Dimensional Time–of–Flight MR Angiography with Timed Injection of Contrast Material", Kanal et al., Radiology 1991; vol. 181(p), 119 (abstract 169C).

"Fast Three–Dimensional Time–of–Flight MR Angiography With Contrast Bolus Injection", Talagala et al., SMRI 1992, paper #332.

"Fast RF–spoiled Three–dimensional MR Angiography of Intracranial Vasculature in Scan Times under 1 minute", Talagala et al., Book of Abstracts, SMRM 1991, p. 1021.

"Bolus Triggered Hepatic Helical CT", Laakso et al., American Journal of Radiology, Mar. 1995 p. 116 (Abstract 224).

"Bolus–Triggered CT Angiography—First Clinical Results", Kopka et al., American Journal of Radiology, Mar. 1995, p. 132 (Abstract 271).

"An Extended–Length Coil Design for Peripheral MR Angiography", Rajan et al., Magnetic Resonance Imaging, vol. 9, No. 4, pp. 493–495, 1991.

"Fast MRI turbo–FLASH Sequences in Aortoiliac Disease", Sivanathan et al., The Lancet, vol. 338, pp. 1090–1091, Oct. 26, 1991.

"The Use of Contrast–Enhanced TurboFLASH Sequences in Aorto–Iliac Disease and Their Comparison with Conventional Angiography", Sivanathan et al., SMRM 1992, Berlin, p. 3108.

"Preliminary Study of Pulmonary Three–Dimensional Time of Flight MR Angiography with Breath–Holding Using a Contrast Medium", Isoda et al., Radiation Medicine, vol. 11, No. 5, Sep.–Oct. 1993, pp. 191–195.

"Dynamic Three–dimensional Imaging with Partial K–Space Sampling: Initial Application for Gadolinium–enhanced Rate Characterization of Breast Lesions", Chenevert et al., Radiology 1995, vol. 196, pp. 135–142.

"Smartprep: A Technique for Improving Hepatic Imaging with Helical CT", Silverman et al., Radiology Supplement, Nov. 1994, p. 165 (abstract 260C).

"Normal Abdominal Enhancement Patterns with Dynamic Gadolinium–enhanced MR Imaging, Radiology", Mirowitz et al., vol. 180, No. 3, 1991, pp. 637–640.

"A Perspective on K–Space", Mezrich, Radiology 1995 (Annual Meeting, Nov. 26–Dec. 1, 1995); vol. 195, No. 2, pp. 297–315.

"Gadolinium–Enhanced Magnetic Resonance Angiography of Abdominal Aortic Aneurysms", Prince, et al., Journal of Vascular Surgery, vol. 21, No. 4, pp. 656–669, Apr. 1995.

"Breath–Held 3D Gadolinium–Enhanced Renal Artery MRA", Prince et al., Proceedings of SMR, Aug. 1995.

"Measuring Signal Intensity Curves in Both Blood and Tissue During Contrast Agent Administration using a Novel Rapid Interleaved Method", Taylor et al., SMRM Aug. 1993, p. 474.

"The Arterial Concentration of Gd–DTPA can be Monitored Non–invasively", Proc. of SMRM, Aug. 1992, p. 1120.

"Clinical Evaluation of Pulmonary 3D Time–of–Flight MRA with Breath–Holding Using a Contrast Media", Isoda et al., Journal Computer Assisted Tomography, 19(6):911–919, Nov.–Dec. 1995.

"Gd–DTPA Enhanced Multi–slab 3D MR Angiography of Aorto–iliac Arteries", Amanuma et al., SMRM, Aug. 1993, p. 524.

"Three–dimensional MR Angiography (3D–MRA) of Aortic Diseases with Bolus Administration of Contrast Media in a Single Breath–hold", Togami et al., SMRM, Aug. 1994, p. 969.

Dixon, "Simple Proton Spectroscopic Imaging", Radiology, Nov. 25, 1984, pp. 189–194.

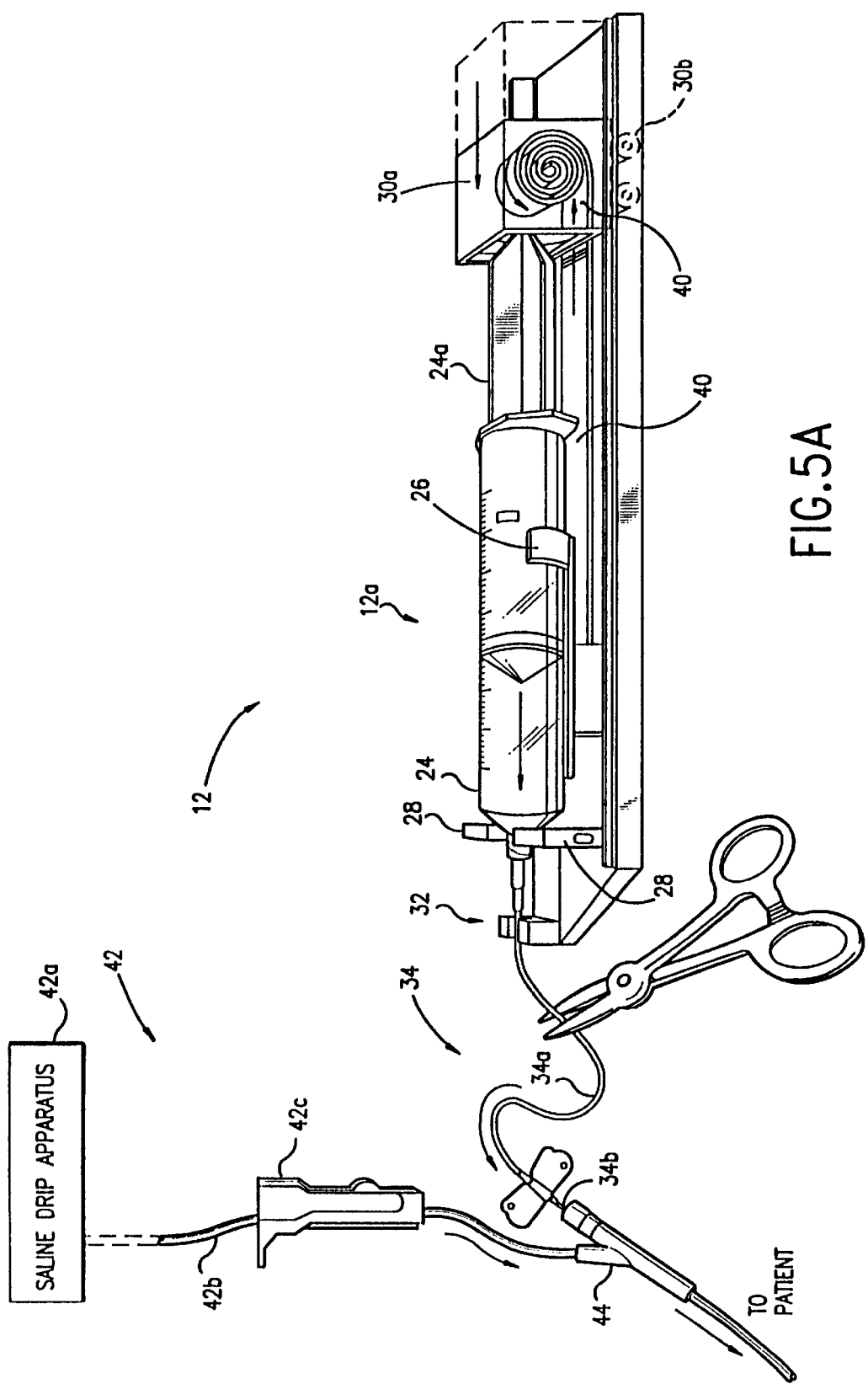

FIG.8A  Pre Gado
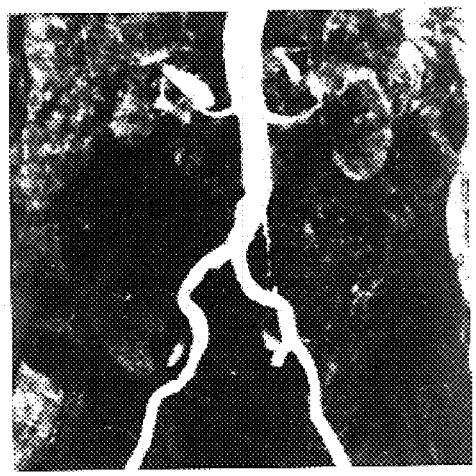
FIG.8B  During Gado Infusion
FIG.8C  Post Gado

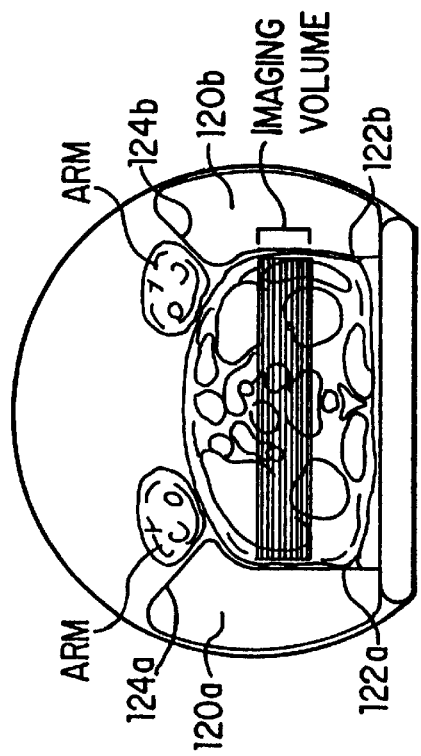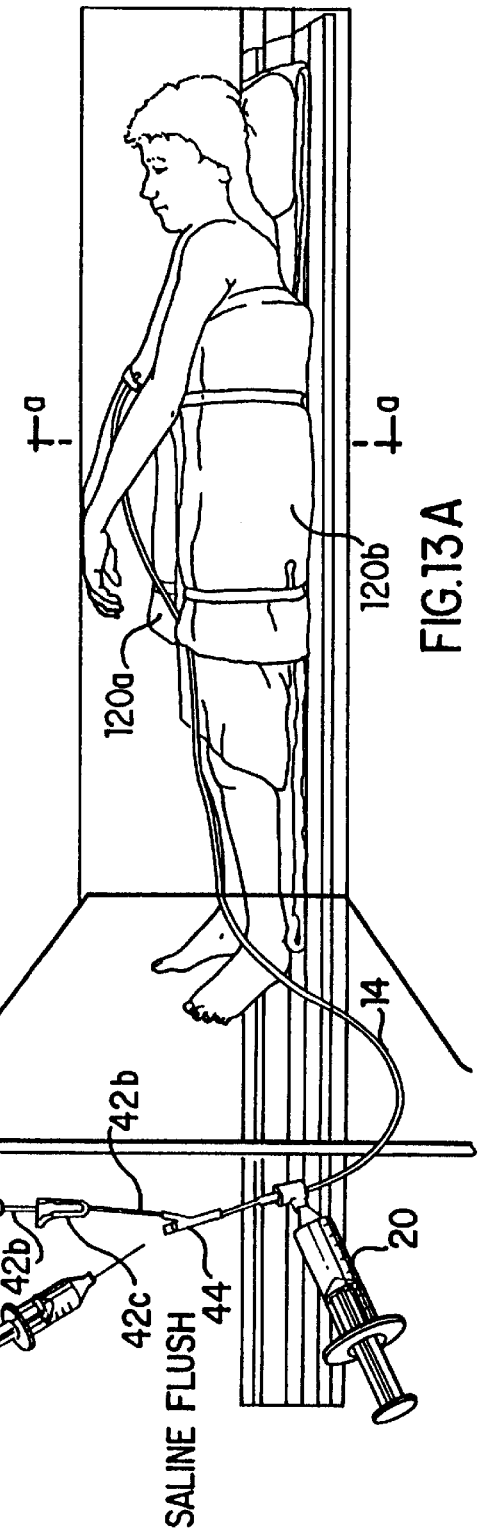
FIG.13B
FIG.13A

METHOD AND APPARATUS FOR MAGNETIC RESONANCE IMAGING OF ARTERIES USING A MAGNETIC RESONANCE CONTRAST AGENT

This application is a continuation of Ser. No. 09/828,429 filed on Apr. 7, 2001, (now U.S. Pat. No. 6,463,318), which is a continuation of Ser. No. 09/124,263 filed on Jul. 29, 1995, now U.S. Pat. No. 6,240,311, which is a continuation of Ser. No. 08/777,347 filed on Dec. 27, 1996, now U.S. Pat. No. 5,792,056, which is a continuation of Ser. No. 08/580, 195 filed on Dec. 28, 1995, now U.S. Pat. 5,590,654, which is a continuation-in-part of Ser. No. 08/420,815 filed on Apr. 12, 1995, now U.S. Pat. No. 5,579,767, which is a continuation-in-part of Ser. No. 08/378,384 filed on Jan. 25, 1995, now U.S. Pat. No. 5,553,619; which is a continuation-in-part of Ser. No. 08/071,970 filed on Jun. 7, 1993, now U.S. Pat. No. 5,417,213.

BACKGROUND OF THE INVENTION

This invention relates to a method of, and apparatus for use in, magnetic resonance imaging; and more particularly, to contrast agent enhanced magnetic resonance angiography for examining, detecting, diagnosing, and treating arterial diseases and injuries, including defining anatomic features relevant to performing aorta and aortic surgery for aneurysmal disease.

Arterial diseases and injuries are common and often have severe consequences including death. Imaging arteries serves to detect and characterize arterial disease before these consequences occur as well as defining anatomic features to assist in performing surgery for aneurysmal disease.

A conventional method of arterial imaging includes inserting a catheter into the artery of interest (the artery under study) and injecting radiographic contrast, for example, an iodinated contrast, while taking radiographs of the artery. Radiographs are commonly referred to as X-rays. In this technique, the contrast remains in the arteries for a few seconds during which the arteries appear distinct from both the veins and background tissue in the radiographs.

Although a catheter-based contrast arteriography technique generally provides high quality arterial images, there is a risk of arterial injury or damage by the catheter and its insertion. There may be thrombosis, dissection, embolization, perforation or other injury to the artery itself. Furthermore, such a technique may result in a stroke, loss of a limb, infarction or other injury to the tissue supplied by the artery. In addition, hemorrhage at the catheter insertion or perforation sites may require blood transfusions. Moreover, kidney failure and brain injury may result from the toxic effects of the X-ray contrast.

More recent techniques of arterial imaging are based upon detecting the motion of the blood within the arteries and/or veins. These techniques involve employing magnetic resonance imaging (MRI) to image moving blood distinct from stationary background tissues. (See, e.g., Potchen, et al., eds., "Magnetic Resonance Angiography/Concepts and Applications", Mosby, St. Louis, 1993; the text of which is incorporated herein by reference). Such techniques do not necessitate catheter insertion into the artery. These techniques are commonly known as 2D time-of-flight, 3D time-of-flight, MOTSA, magnitude contrast, phase contrast, and spin echo black blood imaging.

With pre-saturation pulses it is possible to primarily image blood flowing in one direction. Since arteries and veins generally flow in opposite directions, these pre-saturation pulses allow preferential visualization of the arteries or the veins. Because these techniques depend upon blood motion, the images are degraded in patients who have arterial diseases which decrease or disturb normal blood flow. Such types of arterial diseases that decrease or disturb normal blood flow include aneurysms, arterial stenoses, arterial occlusions, low cardiac output and others. The resulting lack of normal blood flow is particularly problematic because it is those patients with disturbed blood flow in whom it is most important to acquire good quality arterial images.

A related MRI technique relies on differences in the proton relaxation properties between blood and background tissues. (See, e.g., Marchal, et al., in Potchen, et al., eds., supra, pp. 305–322). This technique does not depend upon steady blood in-flow. Instead, this MRI technique involves directly imaging the arteries after administering a paramagnetic contrast agent. Here, after administering the contrast agent, it is possible to image arteries directly based upon the blood relaxation properties. This technique overcomes many of the flow related problems associated with MRI techniques which depend upon blood motion.

Several experts have performed magnetic resonance arterial imaging using intravenous injection of gadolinium chelates (paramagnetic contrast agents). These experts have reported their results and conclusions. In short, these results have been disappointing and, as a result, the use of gadolinium for imaging arteries has not been adopted or embraced as a viable arterial imaging technique. The images using this technique are difficult to interpret because the gadolinium tends to enhance both the arteries and the veins. Since the arteries and veins are closely intertwined, it is extremely difficult to adequately evaluate the arteries when the veins are visible. Further, the difficulty in interpretation is exacerbated as a result of contrast leakage into the background tissues.

However, MRI has evolved over the past decade to become an accepted technique to image the abdominal aorta and abdominal aortic aneurysms. Advances in magnetic resonance imaging for vascular imaging, known as magnetic resonance angiography, have enabled the additional evaluation of aortic branch vessels. However, limitations in magnetic resonance angiography imaging of the slow, swirling flow within aneurysms, turbulent flow in stenoses, and tortuous iliac arteries have limited the usefulness of these general studies in providing detailed information necessary for preoperative planning. In spite of these limitations, recent developments in gadolinium-enhanced magnetic resonance angiography have overcome several of the imaging problems. (See, e.g., Debatin et al., "Renal magnetic resonance angiography in the preoperative detection of supernumerary renal arteries in potential kidney donors", Invest. Radiol. 1993;28:882–889; Prince et al., "Dynamic gadolinium-enhanced three-dimensional abdominal MR arteriography", JMRI 1993;3:877–881; and Prince, "Gadolinium-Enhanced MR Aortography", Radiology 1994;191(1):155–64).

There exists a need for an improved method of magnetic resonance angiography which provides an image of the arteries distinct from the veins and which overcomes the limitations of other techniques. Further, there exists a need for an apparatus which facilitates providing an image of the arteries distinct from the veins and which may be implemented in overcoming the limitations of other techniques.

In addition, there exists a need for contrast (e.g., gadolinium) enhanced magnetic resonance angiography of abdominal aortic aneurysms to provide essential and accurate anatomic information for aortic reconstructive surgery devoid of contrast-related renal toxicity or catheterization-related complications attending conventional arteriography.

SUMMARY OF THE INVENTION

In one principal aspect, the present invention is a method of imaging an artery of a patient using magnetic resonance imaging. The method includes the steps of detecting an elevated concentration of magnetic resonance contrast agent in the artery and imaging at least a portion of the artery including collecting image data which is representative of the center of k-space after detecting the elevated concentration of magnetic resonance contrast agent in the artery.

In one embodiment of this aspect of the invention, image data which is representative of the center of k-space may be collected when a concentration of the contrast agent in the artery is substantially higher than a concentration of the contrast agent in veins adjacent to the artery. In another embodiment, this image data may be collected when the concentration of the contrast agent in the artery is greater than a predetermined concentration. In yet another embodiment, image data which is representative of the center of k-space may be collected substantially at the beginning of an imaging sequence.

The step of detecting an elevated concentration of magnetic resonance contrast agent in the artery may include measuring a base line signal which is representative of a response of the artery to at least one magnetic resonance radio frequency pulse prior to administering the magnetic resonance contrast agent to the patient.

In one embodiment, the artery may be monitored after administering the contrast agent to the patient to detect the arrival of the contrast agent in the artery. The arrival of the contrast may be indicated by detecting a change in the response of the artery to at least one magnetic resonance radio frequency pulse. This change in the response may be a change in a maximum amplitude of a responsive RF signal or a change in the shape of an envelope of a responsive RF signal.

In another embodiment, image data which is representative of the center of k-space is collected substantially at the beginning of an imaging sequence and while the concentration of the contrast agent in the artery is substantially elevated.

In another principal aspect, the present invention is a method of imaging an artery in a region of interest of a patient using magnetic resonance imaging, comprising the steps of detecting a predetermined concentration of magnetic resonance contrast agent in the artery; and imaging at least a portion of the artery including collecting image data which is representative of the center of k-space after detecting the predetermined concentration of the contrast agent in the artery and while the concentration in the artery is higher than a concentration of the contrast agent in veins adjacent to the artery.

In one embodiment of this aspect of the invention, the technique detects the arrival of the contrast in the artery. In this embodiment, image data which is representative of the center of k-space may be collected substantially at the beginning of a 3D imaging sequence.

In another embodiment, image data which is representative of the center of k-space is collected while the concentration in the artery is substantially higher than a concentration of the contrast agent in veins adjacent to the artery. In this embodiment, the step of detecting magnetic resonance contrast agent in the artery includes detecting a substantially elevated concentration of magnetic resonance contrast agent in the artery and the step of imaging at least a portion of the artery includes collecting image data which is representative of the center of k-space after detecting the substantially elevated concentration of magnetic resonance contrast agent in the artery.

In one embodiment, the magnetic resonance contrast agent is administered to the patient by bolus type injection. Under this circumstance, image data which is representative of the center of k-space is collected substantially at the beginning of a 3D imaging sequence.

In yet another principal aspect, the present invention is an apparatus for imaging an artery in a region of interest of a patient using magnetic resonance imaging. The apparatus includes detecting means for detecting a predetermined concentration of magnetic resonance contrast agent in the artery and, in response thereto, for generating an imaging initiation signal. The apparatus also includes imaging means, coupled to the detecting means, for collecting image data which is representative of the center of k-space in response to the imaging initiation signal.

In one embodiment of this aspect of the invention, the imaging means collects the image data which is representative of the center of k-space substantially at the beginning of a 3D imaging sequence. In another embodiment, the detecting means generates the imaging initiation signal when the concentration of the contrast agent in the artery is substantially elevated.

Finally, in another principal aspect, the present invention is an apparatus for imaging an artery of a patient using magnetic resonance imaging and a magnetic resonance imaging contrast agent, comprising, detecting means for generating an imaging initiation signal in response to detecting the magnetic resonance imaging contrast agent in the artery; and imaging means, coupled to the detecting means, for collecting image data which is representative of the center of k-space in response to the imaging initiation signal.

The imaging means may collect image data which is representative of a periphery of k-space after collecting image data which is representative of the center of k-space.

The present invention overcomes the limitations of other techniques by injecting magnetic resonance contrast agents and collecting image data in such a manner that the contrast level in the arteries is higher than that in surrounding veins and background tissue during collection of image data, including data which is representative of the center of k-space.

A high level of arterial contrast also permits directly imaging the arterial lumen, analogous to conventional arteriography. In short, the present invention is, in comparison or relative to other techniques, a method of magnetic resonance angiography which combines several of the advantages of catheter-based contrast arteriography with the advantages of magnetic resonance imaging while substantially eliminating the disadvantages of each.

BRIEF DESCRIPTION OF THE DRAWINGS

In the course of the detailed description of preferred embodiments to follow, reference will be made to the attached drawings, in which:

FIGS. 3, 4, 5A and 5B, and 6A–C are block diagram representations of mechanical infusion devices and configurations, according to the present invention;

FIGS. 8A–C illustrate typical coronal maximum intensity projection (MIP) collapse images obtained (FIG. 8A) prior to injection of gadopentetate dimeglumine, (FIG. 8B) dynamically during intravenous injection of gadopentetate dimeglumine, 0.2 millimoles/kilogram over 5 minutes, and (FIG. 8C) immediately following injection of gadopentetate dimeglumine;

FIG. 13A is an illustration of the appendage cushions in relation to a patient and in conjunction with a portion of the infusion system; and FIG. 13B is a cross-sectional view of the appendage cushions of FIG. 13A taken along line a—a.

DETAILED DESCRIPTION

Figure 1:
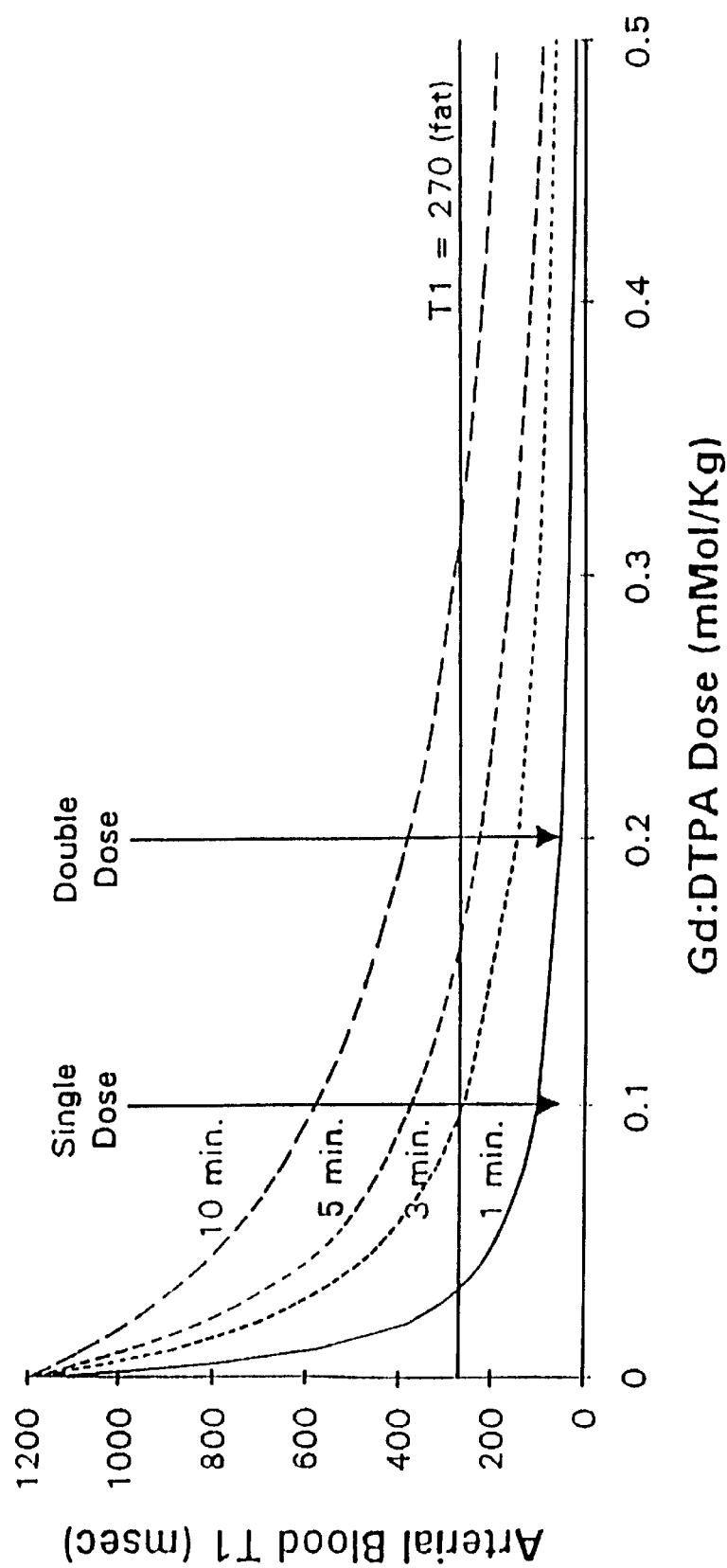
FIG. 1 illustrates longitudinal relaxation time (T1) of blood as a function of injection imaging time and total paramagnetic contrast dose for a compound with a relaxivity of about 4.5/millimolar-second.

The present invention is a system and technique for providing preferential enhancement of arteries relative to adjacent veins and background tissue by correlating the collection of a predetermined portion of data of a magnetic resonance contrast image with the arterial phase of the magnetic resonance contrast enhancement. The arterial phase of the contrast enhancement may be described as a period of a maximum, elevated, and/or substantially elevated contrast concentration in the artery (arteries) relative to adjacent veins. The arterial phase of contrast enhancement may also be described as a period during which the concentration of contrast agent in the artery of the region of interest is about a factor of two greater than a base line or pre-injection response from the region of interest (i.e., the response of the region of interest to a series of magnetic resonance pulses prior to administration of a magnetic resonance contrast agent to the patient).

The system and technique of the present invention synchronizes the collection of a predetermined portion of image data with the arterial phase of contrast enhancement. The present invention includes a detection system, a magnetic resonance imaging system and an infusion system. The detection system monitors and detects the relative concentration of magnetic resonance contrast agent in the region of interest (artery and tissues in a region of interest). The imaging system collects image data which is used in generating a magnetic resonance image of the region of interest. The imaging system may be any suitable magnetic resonance imaging system. Finally, the infusion system administers the magnetic resonance contrast agent to the patient in a controlled manner.

Briefly, by way of overview, the detection system facilitates precise synchronization between the collection of a predetermined portion of image data and a portion of the arterial phase of contrast enhancement. Here, the detection system compares the response of a region of interest before the administration of magnetic resonance contrast agent (e.g., gadolinium) to the patient to the response of the region of interest during and/or after administration of the contrast agent. When a characteristic change in the response to the magnetic resonance pulse is measured by the detection system, the imaging system collects a predetermined portion of image data (e g., data representative of the center of k-space).

In particular, prior to administration of a magnetic resonance contrast agent, the imaging system applies a series of magnetic resonance pulses (radio frequency pulses) to a region of interest in the patient. The detection system measures or determines a base line or pre-contrast response of the region of interest (artery and/or tissues in the region of interest) to that series of pulses. The series of magnetic resonance pulses are applied to the patient to tip the longitudinal magnetization of protons in the region of interest and measure the response of the region of interest before administration of the contrast agent to the patient. The response signal (in the radio frequency range) from the region of interest is monitored using a variety of coils of the magnetic resonance imaging system and measured by the detection system.

After the base line or pre-contrast response is measured, the contrast agent may be administered to the patient. Thereafter, the detection system measures (continuously, periodically or intermittently) the response from the region of interest to detect the "arrival" of the contrast agent in the region of interest. In this regard, the imaging system applies a series of magnetic resonance pulses and the detection system evaluates the response from the region of interest. When contrast agent "arrives" in the region of interest (artery or arteries of interest), the detection system detects a characteristic change in the response from the region of interest to the magnetic resonance pulses; that is, the detection system identifies a characteristic change in the radio frequency signal emitted from the region of interest. This characteristic change in radio frequency signal from the region of interest indicates that the contrast agent has "arrived" in the artery/arteries in that region.

In those instances where the injection of the contrast agent is of a bolus type (i.e., rapid injection), the characteristic change in the response to the magnetic resonance pulses may indicate that the region of interest is in or is "entering" the arterial phase of the magnetic resonance contrast enhancement. Where the contrast agent is injected over a substantial portion of the imaging sequence, detecting the arrival of the contrast agent may indicate that the region of interest is entering the arterial phase of contrast enhancement or will be entering the arterial phase some time in the future depending on a "time delay" as described below.

In one preferred embodiment, the detection system, upon sensing the region of interest is in the arterial phase of contrast enhancement (e.g., contrast concentration in the region of interest is above a predetermined level or the contrast concentration in the artery is greater than that in the surrounding tissues), may instruct the magnetic resonance imaging system to initiate acquisition of the predetermined portion of the imaging data (e.g., data representative of the center of k-space). The concentration of the contrast in the region of interest may be detected in a number of different ways including, for example, a change in the shape of the responsive radio frequency signal, a change in the shape of the signal envelope and/or a change in its amplitude.

In another embodiment, an operator may observe a change in the shape of the radio frequency signal envelop and/or a change in its amplitude measured by the detection system. In response, the operator may instruct the imaging system to initiate an imaging sequence including collecting a predetermined portion of the image data by the magnetic resonance imaging system. In this embodiment, the operator monitors the detection system to observe the characteristic change in the response from the region of interest to the plurality of pulses from the imaging system; and, upon observing such a change, the operator may engage the imaging system to begin collecting image data of the predetermined imaging sequence.

In one preferred embodiment, the predetermined portion of image data is data which is representative of the center of k-space (i.e., the low spatial frequency MR image data), or a portion thereof.

Under the circumstances where the detection system (or operator) instructs the imaging system to collect image data which is representative of the center of k-space upon detecting the start of the arterial phase of contrast enhancement, the magnetic resonance imaging pulse sequence may be arranged such that the central portion of k-space data is collected in the beginning or near the beginning of the sequence and the periphery of k-space is collected thereafter. This provides proper synchronization between the arterial phase of contrast enhancement and the collection of image data which is representative of the center of k-space. Moreover, arranging the sequence such that the central portion of k-space data is collected in the beginning or near the beginning of the sequence insures that a sufficient amount of data which is representative of the center of k-space is collected during the arterial phase of contrast enhancement.

In those instances where the arterial phase is "long", there may be time to collect the entire image data set during the arterial phase. However, in those instances where the arterial phase is brief, collection of image data which is representative of the center of k-space is synchronized with the period of a maximum, substantially elevated, or an elevated contrast concentration in the artery/arteries of interest relative to adjacent veins.

Where the magnetic resonance pulse sequence is of conventional, sequential type and the data representative of the center of k-space is collected in the middle of the scan, the detection system may be employed to determine a "fine adjust" for the infusion rate of the contrast agent by the infusion system to the patient so that a period of maximum, substantially elevated or elevated concentration of contrast agent in the region of interest is correlated to the collection of image data which is representative of the center of k-space (i.e., mapping of k-space). In this embodiment, the detection system monitors the response of the region of interest to a series of magnetic resonance detection pulses. When the detection system determines that the contrast has "entered" the region of interest, the detection system (or operator) may adjust the rate of injection of the contrast agent in order to provide sufficient or maximum overlap between the collection of k-space and the arterial phase of the contrast enhancement. The detection system (or operator) calculates an adjustment to the rate of infusion based on several factors including the time between the start of the infusion and the detection of a change in the response by the region of interest to the magnetic resonance detection pulses ("circulation time delay"), the timing of the mapping of k-space, and the current and future rates of infusion. The detection system (or operator) may accordingly increase or decrease the rate of injection to compensate for the "time delay" in order to provide sufficient or maximum overlap between the mapping of k-space and the arterial phase of contrast enhancement.

In one embodiment, the monitoring and detecting functions of the detection system and imaging system of the present invention may be deferred until the contrast agent is expected in the region of interest. In this regard, the application of the detection pulses (by the imaging system) employed to detect/monitor the "arrival" of the contrast agent to the region of interest, may be delayed according to the time delay expected between the infusion of the contrast to when the contrast "enters" the artery of interest. This will confine the use of the detection system and the magnetic resonance imaging system to those instances when the contrast agent is expected in the region of interest or when a maximum, elevated or substantially elevated contrast agent concentration is anticipated. This may be useful when patients need to hold their breath for the entire period of detection and monitoring.

The present invention is well suited for collecting image data for imaging an artery, including the aorta. In this regard, as described and illustrated at length in the related applications indicated above (which applications are expressly incorporated herein by reference), correlating a maximum, elevated and/or substantially elevated contrast concentration in the artery of interest with the collection of image data representative of the center of k-space enhances the image of that artery. The present invention allows for accurately detecting a maximum, elevated or substantially elevated contrast concentration in the artery of interest relative to surrounding tissues. This facilitates proper correlation between the collection of image data representative of the center of k-space and the arterial phase of contrast enhancement in the artery of interest.

Further, as noted in the related applications, the time between contrast injection and a maximum, elevated or substantially elevated contrast concentration in the artery of interest may vary according to a number of factors including the location of the artery of interest, the size of the artery of interest, the physical condition of the patient, and the time delay due to the configuration of the contrast agent delivery system. These factors may not be precisely quantifiable for each and every patient; and, as a result, it may be difficult to predict (with sufficient precision) for each patient when the period of arterial phase of contrast enhancement occurs in relation to the mapping of k-space. Thus, it may be difficult to precisely time the contrast injection and the imaging sequence to properly capture a sufficient amount of the predetermined image data (e.g., data representative of k-space) during the arterial phase of the enhancement of the region of interest. Indeed, in some instances, there may be a tendency to use more contrast agent than is necessary in order to allow for a longer bolus injection which would ensure that the arterial phase is of sufficient duration to overlap with the collection of image data representative of the central k-space.

Typically, the delay from the time of administering the contrast agent at a maximum, elevated, or substantially elevated rate to the realization of the arterial phase of contrast enhancement in the region of interest may be about 10–50 seconds. Such a large range of time delays may make it difficult to provide sufficient overlap of the arterial phase of contrast enhancement of the region of interest and the collection of image data representing the center of k-space. The present invention, however, "automatically" correlates a period of maximum, elevated or substantially elevated arterial contrast concentration with the mapping of the center of k-space; that is, the detection system synchronizes the collection of image data representative of the center of k-space with a period of maximum, elevated or substantially elevated arterial contrast in the artery of interest. This eliminates the need to use "extra" contrast agent to compensate for possible timing errors.

In short, the present invention alleviates any difficulties in collecting image data corresponding to the center of k-space during the arterial phase of contrast enhancement of the region of interest. Moreover, the present invention insures that the arterial phase of contrast enhancement extends for a sufficient period of the collection of image data representing the center of k-space without "wasting" any contrast agent.

The present invention may be employed in a method and apparatus which provides anatomic information, in the form of images, using a combination of a plurality of magnetic resonance angiography sequences, including one spin-echo and four magnetic resonance agent (e.g., gadolinium) enhanced magnetic resonance angiography sequences. The anatomic images may be used in, for example, pre-operative, operative and post-operative evaluation of abdominal aortic aneurysms and/or abdominal aortic aneurysm surgery. The contrast-enhanced magnetic resonance angiography provides sufficient anatomic detail to detect aneurysms and all relevant major branch vessel abnormalities seen at angiography or at operation.

An evaluation of abdominal aortic aneurysms and other vascular pathology may require one, some or all of the following magnetic resonance image sequences:

(1) an initial T1 weighted sequence; the T1 sequence may be used to identify the location of the aneurysm. This sequence may also be employed to define the location of renal and splanchnic arteries for planning higher resolution gadolinium-enhanced sequences (discussed below). Further, the T1 sequence may provide information as to the approximate size of each kidney, the size of the aneurysm, and the location of the left renal vein. A preferred orientation of this sequence is in the sagittal plane;

(2) a dynamic gadolinium-enhanced 3D volume sequence; the 3D volume sequence may be obtained in the coronal plane and reconstructed into sagittal, axial and/or oblique projections to produce images that are similar to biplane aortography or helical CT angiography. In a preferred embodiment, these images are employed to evaluate the renal and splanchnic artery origins, the iliac arteries, and the distal extent of the aneurysm;

(3 and 4) sagittal and axial 2D time-of-flight images; the sagittal and axial 2D time-of-flight images demonstrate the maximum size of the aneurysm, its proximal extent and peri-aneurysm inflammation. The sagittal and axial 2D time-of-flight images may be employed to detect the presence of thrombus and the features of the thrombus, including its location, surface irregularity and/or enhancement; and (5) 3D phase contrast images; the 3D phase contrast volume images defines the renal arteries in greater detail to facilitate grading the severity of occlusive lesions.

In addition, in one embodiment, the present invention may be implemented in a technique and apparatus wherein a combination of gadolinium-enhanced magnetic resonance angiographic sequences are used to provide a highly accurate mechanism for detecting, examining and grading occlusive lesions. Such information is valuable during many stages of evaluation of the patients.

EXAMPLE 5, set forth in detail below, defines the imaging parameters of the magnetic resonance image sequences (initial sagittal T1 sequence, dynamic gadolinium-enhanced 3D volume sequence, sagittal and axial 2D time-of-flight images, and 3D phase contrast images).

The sequence of imaging the abdominal aorta, as outlined above, may be employed in different combinations for providing anatomic images of the aorta. Under some circumstances when imaging abdominal aortic aneurysms, not all of sequences are necessary. An imaging technique using one or several of the sequences may provide limited information of, for example, the distal end of the aneurysm (dynamic gadolinium enhanced 3D volume imaging sequence) and the maximum size of the aneurysm (sagittal and axial 2D time-of-flight images). One skilled in the art would recognize that other permutations of the sequences are possible and the number and combination of the sequences may be tailored according to the information needed or desired.

Further, several of the sequences may be repeated or omitted according to the information desired. In those instances where sequences are repeated, the information collected may be employed to check or verify the imaging results which are obtained from other sequences. Thus, in short, numerous permutations of sequences may be implemented to provide varying degrees of evaluation, as well as certainty, of abdominal aortic aneurysms. A combination of these sequences may be used to evaluate patients suspected of having other pathology, such as renal artery stenosis or mesenteric ischemia.

The magnetic resonance angiography sequences for generating the image data may be performed during or following infusion of magnetic resonance contrast agent (e.g., gadolinium). Under this circumstance, the system and technique of the present invention may be employed to properly correlate the maximum, elevated or substantially elevated concentration of contrast in the region of interest with the collection of image data representative of the center of k-space. Employing the technique and system of the present invention, the mapping of k-space of one or more of the magnetic resonance angiography sequences may be precisely correlated with the time at which the region of interest possess a maximum, elevated or substantially elevated contrast concentration. Thus, it may be unnecessary to "manually" calculate the proper correlation of a maximum, elevated or substantially elevated rate of infusion and the mapping of k-space according to the location of the artery of interest, the size of the artery of interest, the physical condition of the patient, the time delay due to the configuration of the contrast agent delivery system, and/or the type of pulse sequence employed by the imaging apparatus In a preferred embodiment, the magnetic resonance contrast agent is administered in a vein which is remote from the artery in the region of interest (i.e., the artery under study). The magnetic resonance contrast agent may be injected using a number of different parameters, systems and/or techniques.

In one embodiment, the magnetic resonance contrast agent may be injected into a patient (a human or other animal) for example, substantially throughout the period of imaging in a controlled manner (i.e., injected at a controlled rate over the period of imaging). A substantial portion of the data collection time is a majority of the time and should include the period of time during which the center of k-space is acquired. Under this circumstance, as mentioned above, the detection system may be employed to adjust the rate of infusion of the infusion device to precisely correlate a period of maximum, elevated or substantially elevated arterial contrast concentration in the region of interest with the mapping the center of k-space. In this embodiment, the detection system detects the arrival of the contrast agent in the region of interest and, in response, adjusts the rate of injection of the contrast so that when the imaging system collects image data which is representative of the center of k-space, the region of interest has a maximum, elevated or substantially elevated concentration of contrast. That is, the detection system "fine tunes" the rate of injection of contrast so that the desired arterial contrast concentration occurs while mapping the center of k-space. Thus, the detection system of the present invention insures that the region of interest is in the arterial phase of contrast enhancement during at least a portion of the collection of image data representing the center of k-space.

In another embodiment, the injection is a bolus type (i.e., rapidly). Under this circumstance, in a preferred embodiment, the detection system detects a characteristic change in the response by the region of interest and, in response thereto, instructs the imaging system to collect image data which is representative of the center of k-space. The imaging system collects the image data corresponding to the center of k-space in the beginning or near the beginning of the scan.

The present invention may utilize a number of different magnetic resonance contrast agents. In this regard, the magnetic resonance contrast agents are well known in the art, and are disclosed in, for example, U.S. Pat. Nos. 5,141,740; 5,078,986; 5,055,288; 5,010,191; 4,826,673; 4,822,594; and 4,770,183, which are incorporated herein by reference. Such magnetic resonance contrast agents include many different paramagnetic contrast agents, for example, gadolinium compounds. Gadopentetate dimeglumine, gadodiamide and gadoteridol are paramagnetic gadolinium chelates that are readily available, and which rapidly redistribute into the extracellular fluid compartment. Other gadolinium compounds are acceptable, and may have a higher relaxivity, more rapid redistribution into the extracellular fluid compartment, and greater and faster extraction in the capillary bed. It should be noted that contrast agents that are extracted or degrade in or near the capillary bed are preferred for the present invention.

In one preferred embodiment, when performing at least one of the magnetic resonance angiography sequences, the injected contrast agent should be sufficiently small to rapidly redistribute into the extracellular fluid compartment in the systemic capillary bed, or the contrast agent should be actively extracted from the circulation in the capillary bed distal to the artery of interest, or both. Under these circumstances, the artery (or arteries) of interest contains a high concentration of contrast and the vein (or veins) adjacent to the artery (or arteries) of interest possesses a lower contrast concentration. Further, under these circumstances, the relationship of artery-to-venous contrast concentration is substantially maintained over the period of contrast injection.

Matching the duration of the injection with the time required for a longitudinal relaxation time (T1) weighted magnetic resonance image data set, may provide the situation where it is possible to view the arteries distinct from the veins. Further, by injecting the contrast at a sufficient rate, the longitudinal relaxation time of the arterial blood may be made sufficiently short when compared to that of the background tissues. As a result, the image of the arteries is distinct from background tissue as well.

As mentioned above, an advantage of the present embodiment is the precise accuracy in synchronizing the collection of the center of k-space with a maximum or elevated concentration of the contrast agent in the artery of interest—for each and every scan or sequence. Compensating for the timing of the infusion of the magnetic resonance contrast agent may be unnecessary since the detection system identifies when the artery of interest includes a maximum, elevated or substantially elevated arterial contrast concentration. Thus, employing the detection technique of the present invention alleviates the need to "manually calculate" the correlation of the maximum or elevated rate of infusion with the mapping of k-space accounts for the time delay due to the contrast agent delivery system (e.g., the length of catheter which delivers the contrast agent) and/or the time-delay due to the time required for the contrast agent to circulate from the site of injection, through the body, and into the artery of interest.

It should be noted that the center of k-space may be characterized as 10% to 75% of the total k-space data which, as indicated above, corresponds to the lowest spatial frequency information.

It should be further noted that when imaging larger arteries during the magnetic resonance angiography sequence, in a preferred embodiment, an elevated, substantially elevated or maximum concentration of contrast agent in the artery of interest is typically provided for at least 20% of the time during which image data corresponding to the center of k-space is collected; and preferably, an elevated, substantially elevated or maximum concentration of contrast in the artery of interest is maintained for between 20% to 50% of the mapping of the center of k-space. This, translates into correlating a period of substantially elevated or maximum rate of injection with the period of collection of image data corresponding to the center of k-space so that during at least 20% of the time of mapping k-space, a substantially elevated or maximum concentration of contrast agent is maintained in the artery of interest relative to adjacent veins; and preferably about 50%.

When imaging smaller arteries, in a preferred embodiment, an elevated or maximum concentration of contrast agent in the artery of interest is provided for greater than 50% of the time during which image data corresponding to the center of k-space is collected; and in a more preferred embodiment, an elevated or maximum concentration of contrast in the artery of interest is maintained for greater than 75% of the mapping of the center of k-space. As a result, where the artery of interest is relatively small, the administration of the contrast agent may include a maximum or elevated rate of injection of the contrast agent of greater than 50% of the time of mapping of the center of k-space; and preferably between 50% to 85%, and most preferably greater than 75%. Under this circumstance, fewer artifacts are observed in the smaller vessels or arteries when the contrast is administered at a maximum or elevated rate over a longer period of the k-space mapping.

Further, during the acquisition of magnetic resonance angiographic image data corresponding to the center of k-space, it may be important to avoid excessively rapid changes in arterial contrast concentration. Rapidly changing blood signal during acquisition of the center of k-space may create image reconstruction artifacts. These artifacts may be minimized when the arterial signal intensity is uniform. Further, these artifacts may be minimized by avoiding rapid changes in the arterial contrast concentration during acquisition of image data and especially during acquisition of the center of k-space.

In those instances where the invention is implemented using paramagnetic contrast agents, in a preferred embodiment, infusion is at a rate that will provide a concentration of the agent in the arteries, such that the arteries will have at least 50% more signal than any background structures, including veins, in the final image. In another preferred embodiment, the concentration of contrast agent will cause the longitudinal relaxation time (T1) of the protons in the arteries to be shorter than protons in any of the background material. Where the contrast agent causes the arteries to appear black in the final image (e.g., where the contrast agent shortens T2*, for example, some Fe powders), the contrast agent should be infused at a rate and amount to insure that the effective transverse relaxation time (T2*) in the arteries is shorter than in any of the background material.

Magnetic Resonance Imaging System

Any magnetic resonance imaging (MRI) system suitable for imaging a portion of an animal body, for example, a human, may be used for acquisition of image data in the method of this invention. In particular, apparatus and imaging methods for magnetic resonance angiography are known in the art (see, e.g., U.S. Pat. Nos. 4,718,424; 5,034,694; and 5,167,232, incorporated herein by reference), and these may be used with the method of MRA with dynamic intravenous injection of magnetic resonance contrast agents taught herein, subject only to the constraints taught below.

The parameters of the imaging method of the magnetic resonance angiography sequences are discussed immediately below with respect to gadolinium chelates. The Examples described thereafter include additional imaging parameters. It should be noted, however, that other magnetic resonance contrast agents may be employed in practicing the present invention including paramagnetic contrast agents, such as those described by Marchal, et al., in Potchen, et al., eds., supra, pp. 305–322, the text of which is incorporated herein by reference.

Injection Parameters

Gadolinium chelates are paramagnetic agents which shorten the longitudinal relaxation time, T1, of blood according to EQUATION 1:

$$\frac{1}{T1} = \frac{1}{1200} + \text{Relaxivity} \times [Gd] \quad (1)$$

where:
(1) the longitudinal relaxation time (T1) of blood without gadolinium is 1200 milliseconds; and
(2) [Gd] is the blood concentration of a gadolinium chelate.

With reference to EQUATION 1, to achieve an arterial blood (T1) that is short compared to adjacent fat (T1=270), it is necessary to substantially elevate the arterial blood concentration of the contrast agent in the artery of interest to be greater than ($\frac{1}{270}$ milliseconds−$\frac{1}{1200}$ milliseconds)/ relaxivity of the contrast agent (or 2.9/seconds*relaxivity). Thus, the artery of interest includes a substantially elevated concentration of the contrast agent when that concentration is greater than 2.9 seconds$^{-1}$ relaxivity$^{-1}$ of the contrast agent.

A substantially elevated rate of infusion provides a substantially elevated concentration of the contrast agent in the artery of interest. That is, a substantially elevated rate of infusion provides an arterial blood concentration of the contrast in the artery of interest which is greater than 2.9 seconds$^{-1}$ relaxivity$^{-1}$ of the contrast.

As reflected in EQUATION 2, below, the arterial blood [Gd] may be expressed in terms of the intravenous injection rate and the cardiac output during dynamic imaging at times short as compared to the recirculation time.

$$[Gd]_{arterial} = \frac{\text{Injection Rate}}{\text{Cardiac Output}} + [Gd]_{venous} \quad (2)$$

As long as the gadolinium chelate is sufficiently small, the gadolinium chelate will rapidly redistribute into the extracellular compartment as it passes through the capillary bed and the venous concentration will be low or negligible compared to the arterial concentration. The relationship between the longitudinal relaxation time of arterial blood and the injection rate may then be determined by combining EQUATION 1 and EQUATION 2, as stated below in EQUATION 3:

$$\text{Injection Rate} = \frac{\left[\frac{1}{T1} - \frac{1}{1200}\right]}{\text{Relaxivity}} \times \text{Cardiac Output} \quad (3)$$

To achieve contrast between arterial blood and background tissue, the longitudinal relaxation time of the arterial blood should be reduced to less than that of the background tissues. Of all types of background tissues, fat (T1=270 msec) typically has the shortest longitudinal relaxation time. Assuming a typical minimum resting cardiac output of 0.0005 Liters/Kg-sec and requiring the longitudinal relaxation time to be less than 270 milliseconds simplifies EQUATION 3 to EQUATION 4 as shown below:

$$\text{Injection Rate} > \frac{0.0015 \text{ L/Kg-sec}^2}{\text{Relaxivity}} \quad (4)$$

By way of example, gadopentetate dimeglumine, gadodiamide, and gadoteridol are three paramagnetic gadolinium chelates that are readily available and rapidly redistribute into the extracellular fluid compartment. The relaxivities of gadopentetate dimeglumine and gadoteridol are about 0.0045/molar-second. Based upon the aforementioned and using EQUATION 4, the minimum injection rate is greater than 0.033 millimole/Kg-minute.

With continued reference to EQUATION 4, a rate of infusion which is greater than 0.0015 Liters/Kg-sec$^2$ divided by the relaxivity may provide a maximum concentration of the contrast agent in the artery of interest. That is, infusing the contrast into the patient at a rate of greater than 0.0015

Liters/Kg-sec$^2$ divided by the relaxivity may yield a maximum arterial blood concentration of the paramagnetic contrast agent.

The total dose of gadolinium chelate required may be determined by multiplying the injection rate by the imaging time. For a relaxivity of 4.5/millimolar-second, and an imaging time of 5 minutes (300 seconds), the dose should substantially exceed 0.1 millimole/kilogram.

The dose of the gadolinium chelate may be within the range of 0.05 millimoles/kilogram body weight to 1 millimoles/kilogram body weight depending upon the time required to obtain the image. It should be noted that the dose of the contrast should not be too high such that there may be undesirable toxicity or T2 effects. In a preferred embodiment, the dose of the gadolinium chelate is within the range of 0.2 millimoles/kilogram body weight to 1 millimoles/kilogram body weight. In a more preferred embodiment, the dose of the gadolinium chelate is about 0.3 millimoles/kilogram body weight.

When injecting by hand or with simple pumps, it may be convenient to give all of the patients the same volume of contrast agent. In this way the operator may get accustomed to timing the injection of a standard infusion volume to provide proper correlation between an elevated concentration of contrast agent in the region of interest to the collection of image data representative of the center of k-space. In those instances where the contrast agent is a gadolinium contrast, a preferred standard volume is 40 to 60 ml.

In those instances where the contrast injection times are longer than the recirculation time, the longitudinal relaxation time of arterial blood tends to be even shorter since a fraction of the gadolinium chelate will recirculate. It should be noted that a T1 of 270 ms (corresponding to the brightest background tissue fat) is equivalent to a gadopentetate dimeglumine concentration of about 0.6 millimole/liter.

FIG. 1 illustrates the longitudinal relaxation time (T1) of blood as a function of infusion time and the total paramagnetic contrast dose for a paramagnetic contrast compound having a relaxivity of 4.5/millimolar-second. An examination of FIG. 1 reveals that the shortest T1 occurs with the shortest infusion time and the largest gadolinium dose. For typical imaging times of 3 to 5 minutes, FIG. 1 further reveals that the dose should be of the order of 0.2 millimoles/kilogram or larger in order to achieve a longitudinal relaxation time of blood significantly shorter than that of the brightest background tissue fat (T1=270) for the entire duration of imaging.

It should be noted that higher doses of gadolinium and gadolinium chelates with higher relaxivity may also improve image quality.

Imaging Parameters

Any suitable T1 weighted magnetic resonance imaging sequence may be used during injection of the paramagnetic contrast. Suitable imaging sequences will be readily apparent to the skilled practitioner and are described in Potchen, et al., eds., supra. The following criteria for selection of preferred imaging parameters are based on experience in over 100 patients on a 1.5 Tesla General Electric signa magnet with version 4.7 or higher software. A three-dimensional Fourier Transform (volume) acquisition (3D FT) is preferred in the abdomen because of its intrinsically high spatial resolution and high signal-to-noise ratio, even with a large, body coil. The gradient echo (gradient recalled) pulse sequences are preferred since they allow a short TR (repetition time) which allows a shorter imaging acquisition time. Short imaging times have the advantage of allowing the same total gadolinium dose to be injected at a faster rate.

Spoiled Versus Non-spoiled Gradient Echo Imaging

It should be noted that one might expect steady state gradient echo imaging (GRASS) to be preferable to the spoiled gradient echo imaging because the long T2 (transverse relaxation time) of blood increases the steady state blood signal. However, this effect enhances veins more than arteries, because the fast, pulsatile flow of arterial blood spoils its steady state component. In theory, this may have the paradoxical effect of reduced arterial contrast. In practice, there may only be a small difference between the spoiled and unspoiled techniques. In patients with slow arterial flow (which is not self-spoiling), a steady state gradient echo pulse sequence may be preferred. A spoiled gradient echo pulse sequence (SPGR) was chosen for most of the studies described herein to simplify the theory and analysis as well as to reduce the potential for differential steady state magnetization between arterial blood, slower venous blood and background tissue.

Echo Time

Because the brightest background tissue is fat, it is preferable to use a TE (echo time) where fat and water are out of phase, thereby achieving an incremental improvement in vessel-to-background contrast. At 1.5 Tesla, this occurs about every 4.6 msec beginning at about 2.3 msec which corresponds to a TE of 2.3, 6.9, 11.5, . . . msec. The shortest of these possible TE values (6.9 or about 2.3 msec in the studies described herein) is preferred. Shorter TE's tend to minimize the effects of motion related phase dispersion.

Repetition Time

In a preferred embodiment, TR should be as short as is possible. A TR of 24–25 msec was the shortest possible on the equipment used for the studies described in EXAMPLES 1–3. As the TR is shortened, the flip angle must be adjusted to maintain the optimal T1 weighing.

Flip Angle

With a gadolinium chelate dose of 0.2 millimoles/kilogram and a 3–5 minute injection time and imaging time, the longitudinal relaxation time of the arterial blood is predicted to be in the order of 150 to 200 milliseconds. It will, however, be shorter as a result of the recirculation time being less than 3–5 minutes. The relative signal intensity, SI, in a 3D FT spoiled gradient echo acquisition as a function of blood T1, TR, T2, T2*, flip angle σ, and proton density N(H) may be expressed as stated in EQUATION 5, below, and calculated accordingly.

$$SI = N(H) \frac{1 - \exp\left(-\frac{TR}{T1}\right)}{1 - \cos(\alpha)\exp\left(-\frac{TR}{T1}\right)} \sin(\alpha)\exp\left(-\frac{TE}{T2^*}\right) \quad (5)$$

Figure 2:
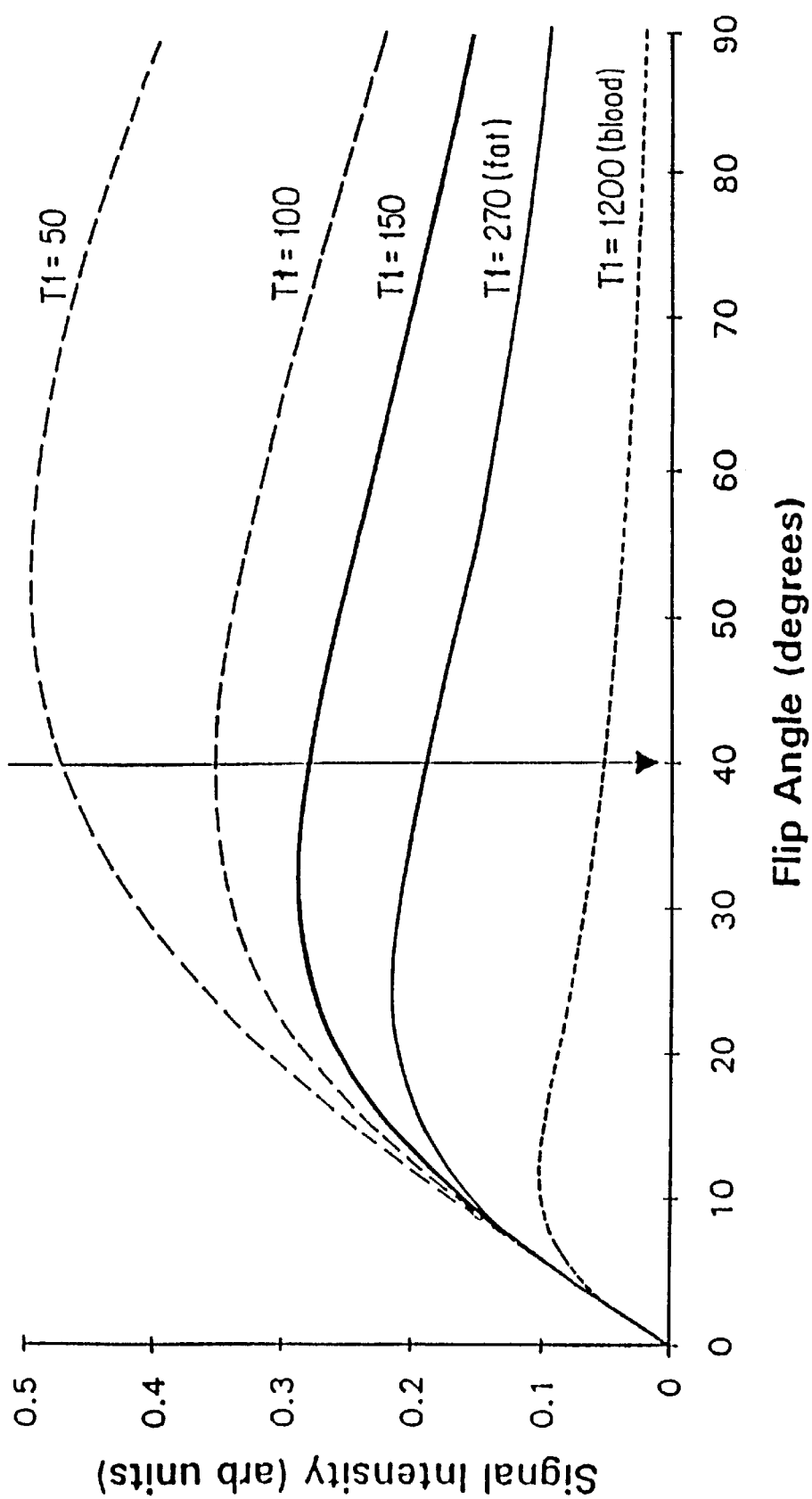
FIG. 2 illustrates calculated magnetic resonance signal intensity as a function of flip angle for 5 different longitudinal relaxation times (T1) assuming a spoiled, 3D volume acquisition with TR equal to 25 msec and TE<<T2*.

FIG. 2 graphically illustrates relative signal intensity for T1 equal to 50, 100, 150, 270 (fat), and 1200 (blood) under the following conditions: (1) TR=25 milliseconds, and assuming TE is small compared to T2* (the observed transverse relaxation time). FIG. 2 reveals that a flip angle of about 40 degrees is optimal for maximizing blood-to-background tissue (fat) contrast when the longitudinal relaxation time (T1) of blood is of the order of 200 milliseconds. For larger gadolinium doses with faster injection rates, a larger flip angle may be more appropriate.

Volume Orientation

In order to minimize the image acquisition time, the imaging volume should be made as thin as possible while containing the arteries of interest. In this regard, it may be useful to orient the image volume for maximum in-plane coverage of the vessels of interest as opposed to the perpendicular orientation required for optimal time-of-flight magnetic resonance angiography. Optimizing the orientation and minimizing the thickness of the imaging volume is facilitated by first acquiring a conventional black-blood or time-of-flight MRI to use as a guide for precise localization. Phase and frequency encoding axes should be oriented such that cardiac and respiratory motion artifacts do not superimpose on the vessels of interest. Generally, for imaging the aorta-iliac system, the imaging volume should be oriented coronally, and the phase encoding axis should be set right-to-left. For imaging the thoracic aorta, a sagittal orientation is preferred and for imaging the subclavian arteries, an axial orientation is preferred.

Partitions

The number of partitions (slices) is determined by the thickness of the image volume divided by the partition thickness. The partition thickness is the image resolution along the axis perpendicular to the plane of the partitions. It may be useful to employ thin partitions in order to have high image resolution. The image acquisition time, however, linearly increases with the number of partitions. As a result, keeping the image acquisition time short requires minimizing the number of partitions.

It should be noted that there may be a loss of signal-to-noise as the voxel size is decreased by using higher resolution pixels. Generally, 0.5 to 3 millimeter resolution with 28 to 60 partitions is adequate for the aorta and major branch vessels. The skilled practitioner will balance the need to increase resolution by decreasing voxel size with the need to avoid excessive periods of time to acquire image data.

Field-of-View

The field-of-view must be made large enough to avoid excessive wrap-around artifact. Wrap around artifacts occur when there are structures outside the field of view along the phase encoding axis. These structures are mapped by the phase encoding process to superimpose on structures within the field of view.

In addition, because of the limited number of pixels along the frequency encoding axis and the time penalty for each additional pixel along the phase encoding axis, it is also desirable to make the field-of-view as small as possible in order to maximize image resolution with the minimum image acquisition time. Generally, for imaging the abdominal or thoracic aorta, a field-of-view of about 36 centimeters is appropriate for most patients. It may be increased for larger patients and reduced for smaller patients. Smaller field-of-views may be used for other parts of the body.

Use of a no-phase wrap algorithm is a less preferred embodiment. Under the circumstance of this invention, this has a disadvantage of generally requiring more imaging time and, as a result, a larger gadolinium dose.

Coils

It is preferable to use the smallest possible coil in order to minimize noise. There is also an advantage to coils that encircle the body part of interest such that the signal will be homogeneous throughout the entire field-of-view. It may be useful to use a coil with quadature.

Patient Positioning

The patient should be positioned such that the body part being imaged remains stationary during the acquisition of image data.

Cardiac and Respiratory Motion Compensation

The phase artifact related to respiratory and cardiac motion may be minimized by combining the T1 weighted imaging sequence with respiratory or electrocardiographic gating. Gating has the disadvantage of increasing the scan time—particularly in patients with irregular rhythms. Compensation techniques in which the acquisition of the image data in k-space is matched to the respiratory and or cardiac cycle may eliminate some phase artifact without significantly increasing the scan time.

In imaging regions of the body that move substantially with respiration (e.g., the renal arteries) it may be useful to acquire data while the patient is holding his breath. This may require shortening the duration of the image acquisition time to under one minute. If the patient cannot hold his breath for the entire period of image acquisition, than it may be useful to hold the breath during acquisition of image data corresponding to the center of k-space and breathing only during acquisition of data corresponding to the periphery of k-space. Examples 6 and 7 discuss the parameters and results of a breath hold imaging technique.

To facilitate breath holding during acquisition of image data which is representative of the central portion of k-space (i.e., the central half of k-space) it may be advantageous to order or arrange k-space centrically or in a shifted fashion so that the center of k-space is acquired in the beginning of the scan. In this way, if the patient begins breath holding at the beginning of the scan, the breath holding will automatically coincide with the collection of image data which is representative of the center of k-space. It may, however, be necessary to have a series of radio frequency pulses precede the center of k-space so that the background tissues reach their equilibrium degree of saturation. A few seconds of radio frequency pulses are sufficient in most cases for the tissues to reach dynamic equilibrium.

Pre-scanning

The pre-scanning process is used to tune to the optimum frequency and to optimize the receiver gain. In the pre-scanning process, it is necessary to compensate for the changes in the patient's magnetic resonance signal that will occur during the contrast injection. In those instances when the paramagnetic contrast agent is a gadolinium chelate, it is preferable to tune to the water peak. About a 20% to 50% margin should be incorporated into the receiver gain setting to allow for increased signal during contrast administration corresponding to contrast arriving in the volume of interest.

Premedication

Premedicating patients with an analgesic or sedative such as diazepam may be useful for at least two reasons. Firstly, it may help the patient to tolerate the claustrophobic sensation of being within the magnet thereby reducing voluntary motion artifacts. Secondly, and more importantly, its relaxation and cardiac depressant effects tend to reduce the cardiac output. A lower cardiac output results in a higher arterial contrast concentration which thereby improves the image quality. This result is opposite from conventional magnetic resonance angiography which is degraded when the cardiac output decreases. By reducing the cardiac and respiratory rates, analgesics and sedatives may minimize the fraction of the image acquisition that is adversely affected by cardiac and respiratory motion artifacts.

Magnetic Resonance Contrast Agents

As mentioned above, many different magnetic resonance contrast agents may be employed when implementing the present invention; for example, numerous paramagnetic contrast agents are suitable. As mentioned above, gadolinium compounds, for example, paramagnetic gadolinium chelates, such as gadopentetate dimeglumine, gadodiamide, and gadoteridol, are readily available and rapidly redistribute into the extracellular fluid compartment. Other gadolinium compounds are acceptable. In general, preferred contrast agents have a high relaxivity, rapid redistribution into the extracellular fluid compartment, and are readily extracted from the capillary bed. It should be noted that, contrast agents that are extracted or degrade in the capillary bed are preferred in the present invention.

In particular, gadolinium chelates are commercially available from such companies as Bracco (under the name "ProHance"), Berlex (under the name "Magnevist"), and Nycomed USA (under the name "OmniScan"). It should be noted that the gadolinium chelate which is commercially available from Nycomed appears to facilitate greater contrast enhancement between the artery and the surrounding veins and tissue.

Overview of Hardware

Figure 11:
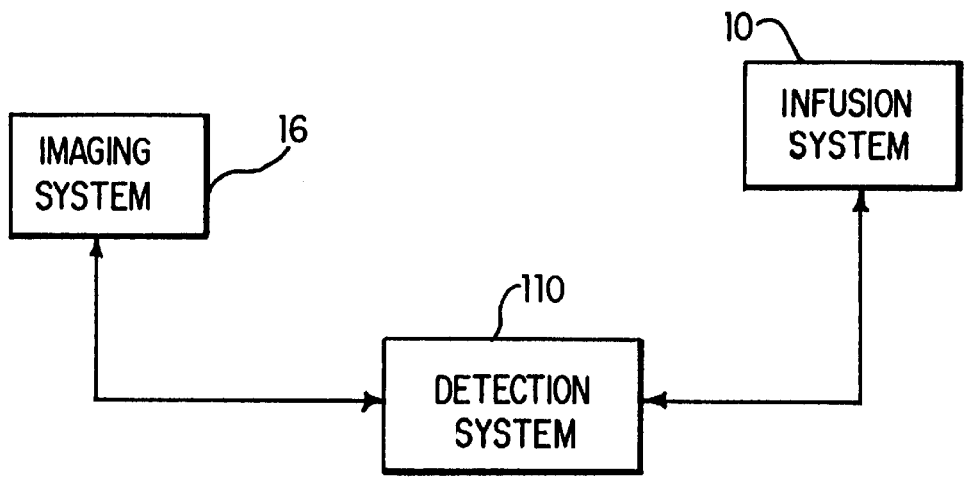
FIG. 11 is a block diagram representation of one embodiment of the present invention (imaging system, infusion system and detection system)

With reference to FIG. 11, the present invention includes an infusion system 10, a magnetic resonance imaging system 16 and detection 110. Briefly, the infusion system 10 includes infusion device 12 and associated hardware which facilitates in the administration of the magnetic resonance contrast agent to the patient. The infusion device 12 may include a syringe or may be a mechanical type device under the control of the detection system 110 and/or an operator. The infusion system 10 is discussed in more detail below.

The magnetic resonance imaging system 16 collects image data which may be used to generate an image of the region of interest. The imaging system 16 may be a commercial magnetic resonance imaging system (including both hardware and software), for example a General Electric Signa Magnet using version 4.7, 5.2, 5.3, 5.4 or 5.5 software) which is suitable for imaging a portion of an animal body, for example, a human. In addition, the software used with the commercial magnetic resonance imaging system may be modified to accommodate several of the embodiments described herein, including collecting image data which is representative of the center of k-space in the beginning of the imaging sequence.

The detection system 110 monitors and detects the arrival of the magnetic resonance contrast agent in the artery and/or tissues in a region of interest. The detection system 110, in a preferred embodiment, monitors the region of interest to correlate collection of image data representative of the center of k-space with a maximum, elevated or substantially elevated concentration in the artery of interest. The detection system 110 is discussed in detail below.

Injection

In a preferred embodiment, the type or form of injection of the paramagnetic contrast is intravenous. The injection of the paramagnetic contrast is performed intravenously in order to eliminate or reduce the complications associated with the catheterization required for arterial injections.

The specific site of injection is important for several reasons. The site of injection should be remote from the "region of interest"; that is, the region that is to be scanned. For example, when imaging the abdominal aorta, intravenous injection of the paramagnetic contrast into an arm vein is preferred (See, FIG. 13B). Use of a leg vein should be avoided. Further, there may be some benefit in avoiding the antecubital fossa because the patient may bend the elbow during a long (3–5 minute) period of injection which may result in extravasation of the contrast into the subcutaneous tissues. As a result, under this condition, a forearm or upper arm vein may be preferable.

It should be noted, however, that when the injection is by rapid infusion (i.e., less than one minute in duration) the antecubital vein may be preferred because of its close proximity to the heart compared to the forearm and hand.

In those instances where an artery in the arm is to be imaged, the site of the injection may be a leg vein or a vein in the opposite arm. Here, the site of injection is remote from the "region of interest", i.e., the artery in the arm.

Moreover, it is important to correlate a maximum, elevated or substantially elevated concentration of contrast agent in the artery of interest relative to adjacent veins with the mapping of k-space. This ensures that the image data representative of the center of k-space is collected over some period during which a maximum, elevated or substantially elevated concentration of contrast agent is maintained in the artery of interest relative to adjacent veins. The detection system (discussed in detail below) monitors the artery of interest so that the collection of image data representative of the center of k-space coincides with an elevated arterial contrast concentration.

Figure 3:
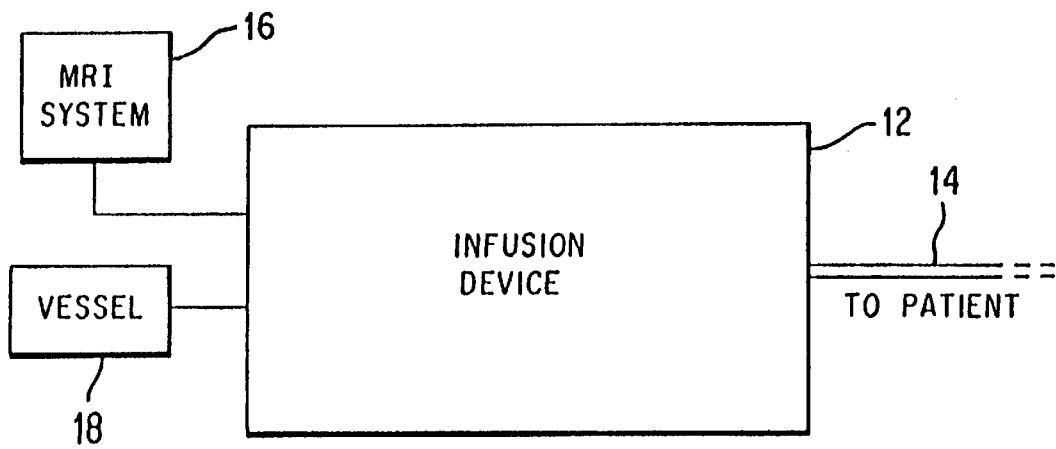
Figure 4:
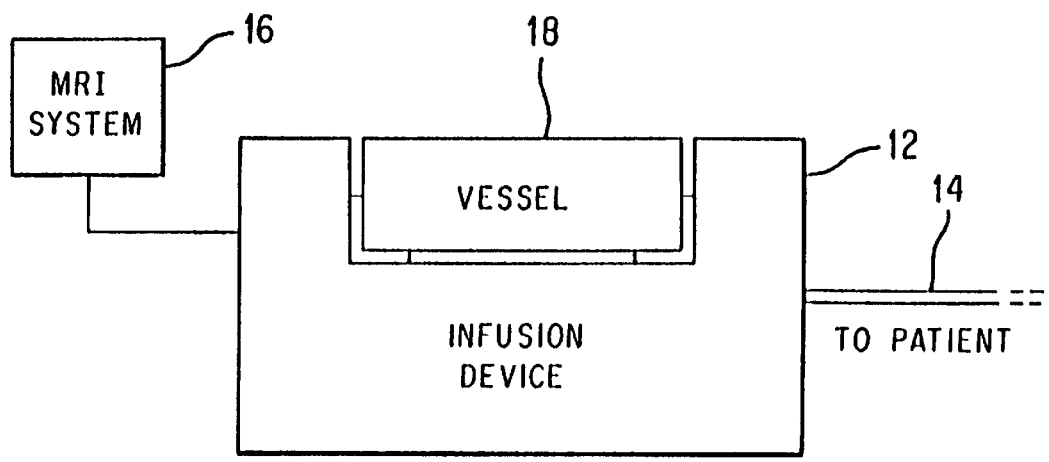

In a preferred embodiment, as illustrated in FIGS. 3 and 4, infusion system 10 includes a mechanical infusion or injection device 12. The infusion device 12 is an automated type of injector having reliable, consistent and controllable operating conditions. The infusion device 12 is employed to inject the magnetic resonance contrast agent into the vein of the patient at an infusion rate sufficient to provide contrast enhancement of an image of an artery relative to veins in the field of view of the magnetic resonance image and substantially throughout the period of acquisition of image data. The infusion device 12 couples to the patient using conventional techniques, for example, appropriately selected tubing 14 which permits fluid flow between the mechanical infusion device 12 and the patient. Such tubing may be, for example, an angiocatheter.

A mechanical injector is preferred over manual/operator injection because of the greater reliability, consistency, and controllability when compared to injecting by hand. Moreover, a mechanical injector facilitates the implementation of a fully automated infusion, imaging and detection system of the present invention. In this regard, the detection system of the present invention may control several of the infusion parameters of the infusion system.

Since the magnetic field interferes with normal functioning of electronic devices, a pneumatic powered, spring loaded or other non-electric pump may be suitable. It should be noted, however, that an electrical pump may be used if its operation is unaffected by the operation of the magnetic resonance imaging system, e.g., if the pump is adequately shielded or if it is located sufficiently far from the magnet.

In one preferred embodiment, the mechanical infusion device 12 is coupled to the magnetic resonance imaging system 16 to facilitate proper or desired timing between the injection of the magnetic resonance contrast agent and the acquisition of the image data, in addition to providing proper or desired rates of infusion of the contrast agent.

In another preferred embodiment, proper or desired timing and rates of infusion of the contrast agent are controlled through a control mechanism in the mechanical infusion device 12. That is, the mechanism that controls the infusion timing and rates of infusion is implemented within the mechanical infusion device 12. In this circumstance, the mechanical infusion device 12 is a "self-contained" unit. For example, the infusion rate may be controlled with an adjustable fluid flow resistor.

As mentioned above, the infusion device 12 injects the magnetic resonance contrast in a controlled manner. The contrast may be contained in a vessel. As illustrated in FIGS. 3 and 4, the mechanical infusion device 12 is coupled to a vessel 18 which contains the magnetic resonance contrast agent. In one embodiment, the vessel may contain a sufficient quantity of contrast agent for one application of the invention or one sequence of the plurality of the magnetic resonance angiography sequences, e.g., a single use vessel. In an alternative embodiment, the vessel may contain a quantity which allows several applications of the invention, e.g., a reservoir type of vessel. As is illustrated in FIG. 3, the mechanical infusion device 12 may be adapted to receive the vessel somewhat like a fountain pen receiving an ink cartridge. In an alternative embodiment, as illustrated in FIG. 4, the infusion device 12 may be coupled to the vessel using conventional methods.

Figure 5B:
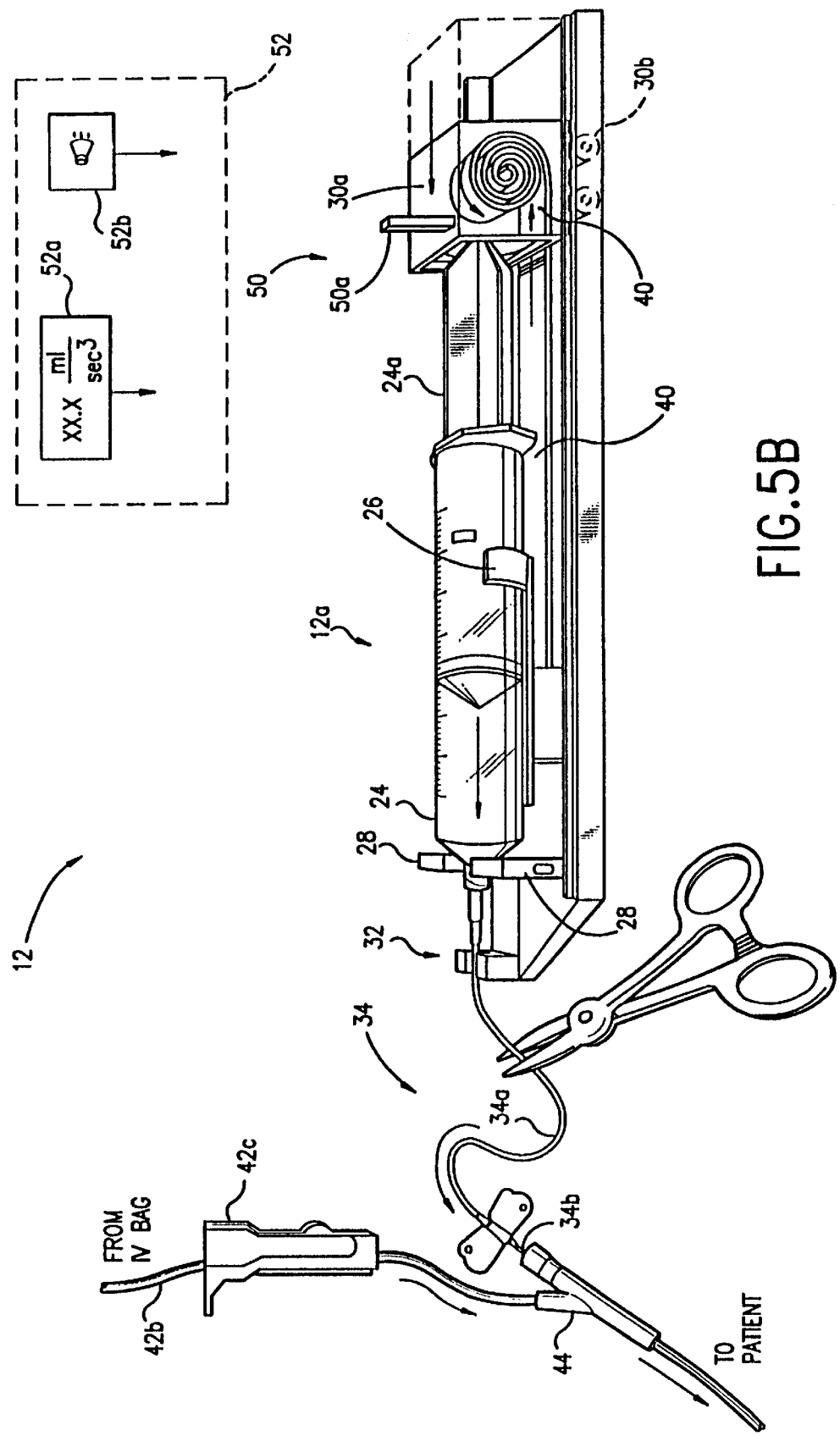

FIGS. 5A and 5B illustrate a mechanical infusion device 12 in more detail. The mechanical infusion device 12 of FIGS. 5A and 5B include several of the components described and illustrated in U.S. Pat. Nos. 4,202,333; 4,298,000; 4,430,079; and 4,597,754. The descriptions of these patents, including several of the components of the mechanical infusion device 12 described therein, are incorporated herein by reference. Moreover, such infusion devices are commercially available from 3M Corporation and their product specification sheets are also incorporated by reference.

In those instances where the mechanical infusion device 12 is employed within the environment of the magnetic field, the infusion device 12 should be fitted or manufactured with magnetic resonance compatible material. For example, the infusion devices which are commercially available from 3M Corp., should be fitted with a magnetic resonance compatible spring. This requires manufacturing the spring from non-magnetic materials, for example, plastic or certain metal alloys such as eljaloy or inconel.

To obtain a constant or variable rate of infusion of the magnetic resonance contrast agent, the device 12 of FIGS. 5A and 5B may include a spring which has a constant width and thickness in order to exert a constant force; or, alternatively, the spring may have a variable width and/or variable thickness to provide a variable spring force. Under this circumstance, the infusion rate may be controlled to be either constant or variable by design of the spring and, in effect, pre-programmed by selection of the spring's design parameters.

In one preferred embodiment, the infusion device 12 may be designed to accommodate a 50 cc syringe having a fluid capacity of 60 cc and containing one dose of the contrast agent. The infusion device 12 may also be designed to permit an external force on the syringe to modify or customize the rate of infusion of the contrast agent. This external force is separate from the force of the spring of the infusion device 12.

Further, the infusion device 12 may include a flow rate indicator 50 (FIG. 5B) to provide an indication of flow rate of the contrast agent to the patient. Under this circumstance, the operator may visually or audibly observe, in a rather simple manner, the rate of flow of the contrast agent. This will allow the operator to exert an external force more accurately (both in the amount of force applied and in a timing sense) thereby facilitating a modification of the predetermined injection rate. Further, in an automated-type of infusion device, the flow rate indicator 50 permits the operator to visually or audibly monitor a "pre-programmed" infusion rate or sequence.

Briefly, with reference to FIG. 5A, the mechanical infusion device 12 further includes syringe 24, a syringe clamp 26, a syringe restraint or stop 28, a block and spring housing 30a, roller bearings 30b, a reflux valve 32 and a catheter 34 having tubing 34a and a needle 34b (butterfly type). The syringe 24 contains the contrast agent to be administered to the patient during magnetic resonance imaging. A plunger 24a of the syringe 24 is engaged by a spring 40 which is housed in the block and spring housing 30a. In operation, the spring 40 engages the plunger 24a to pressurize the syringe 24. The syringe is maintained in a stationary position within the mechanical infusion device 12, and in particular, in housing base 12a, via the syringe clamp 26 and the syringe restraint 28.

In one preferred embodiment, the mechanical infusion device 12 is coupled to a saline drip apparatus 42 (saline drip 42a, tubing 42b and roller clamp 42c). The saline drip apparatus 42 is applied to an input of a y-port connector 44. The syringe 24 is applied to the other input of the y-port connector 44. This conventional configuration facilitates a saline flush following the administration of the contrast agent within the syringe 24. In those instances where the tubing leading from the saline drip apparatus 42 to the y-port connector 44 has a one-way valve to prevent reflux of contrast, it is acceptable to leave the saline drip "on" during infusion. Under this circumstance, as soon as the infusion of the contrast agent is complete, the drip infusion will automatically resume to "flush" gadolinium within the intravenous tubing and deliver the contrast agent which remains in the tubing to the patient.

The rate of injection of the contrast agent from the syringe 24 is determined or controlled, in large part, by the size or gauge of the needle 34b, which functions as a fluid flow restrictor according to Poiseulle's Law. The rate of injection is also controlled by the amount of force that the spring 40 (the restoring force of the spring 40) applies to the plunger 24a of syringe 24, the syringe cross-sectional area, the gadolinium viscosity as follows:

$$\text{Infusion Rate} = \frac{\Pi r^4 F}{8 L \mu A}$$

where:
  r=radius of flow restricting needle lumen;
  F=spring force;
  L=length of flow restricting needle;
  $\mu$=viscosity of the fluid; and
  A=cross-sectional area of the syringe.

Examining the infusion rate equation immediately above reveals that a variation of the syringe size (A), needle length (L), and/or fluid viscosity ($\mu$) impacts the rate of infusion of the contrast agent. The viscosity of the fluid, however, may be dependent on the temperature of the contrast agent (gadolinium chelate). Thus, in those instances where the temperature of the contrast agent alters the viscosity of the contrast, the rate of infusion is also dependent on this "variable."

It should be noted, however, that the influence of viscosity on the flow rate may be substantially reduced by employing a fluid flow restrictor which minimizes the effects of viscosity on the rate of fluid flow.

In one embodiment, the characteristics of the spring 40 (e.g., spring force) may be selected or designed such that the spring 40 applies a constant force upon plunger 24a throughout the period of contrast infusion. In another preferred embodiment, the characteristics of the spring 40 may be selected or designed such that the spring 40 applies a variable force on the plunger 24a. That variable force may correlate with the imaging process so that a maximum or substantially elevated injection rate provides a maximum or substantially elevated concentration of contrast in the artery of interest during the collection of image data which corresponds to the center of k-space.

The rate of injection, however, may be increased or decreased using a manual, spring loaded, or pneumatic/electrical injection rate adjustment mechanism which may be connected to various components of the device 12, including, the spring 40, the block and spring housing 30a, the roller bearings 30b, the plunger 24a, the tubing 34a, and/or the fluid flow restrictor 34b. The pneumatic or electrical type injection rate mechanism may be coupled to the detection mechanism 110 which would permit modification of the rate of injection. This embodiment is described in detail below.

FIG. 5B illustrates a manual injection rate mechanism 50 for allowing the operator to readily alter the rate of injection and thereby modify the rate of injection of the contrast agent to accommodate or implement a desired timing of an elevated or maximum rate of flow of the contrast agent.

The spring force should be sufficient such that the flow restrictor, required to give the desired flow rate, has a flow resistance that is much greater than any flow resistance in the intravenous line. The spring force should not be so high that a person of ordinary strength can not reduce or increase this force when a manual spring adjustment mechanism 50 is designed as the means for adjusting the rate of flow (i.e., the amount of external force applied to the spring) of the contrast agent. In general, a spring with about 5–10 pounds of spring force is suitable for 2–3 minute infusions and a higher spring force may be required for faster infusions. Infusions as short as 30 seconds may require a spring force of 20–30 pounds.

A fluid flow restrictor may be manufactured from, include or be comprised of a needle, a short piece of tubing of narrow calibre (e.g., an intravenous angiocatheter of 20 gauge or larger may be satisfactory), an orifice (for example made of ruby or sapphire), a focal compression of the IV tubing, or other mechanism which impedes the flow of fluid.

It should be noted that a precision orifice may offer several advantages when employed as a fluid flow restrictor. For example, in those instances where an incompressible fluid is to be administered, such as gadopentetate dimeglumine, gadoteridol, or gadodiamide, flow through an orifice is governed by the Bernoulli effect. In this regard, the flow rate of the fluid through the orifice is proportional to the square root of the pressure drop:

$$\text{Infusion Rate} = K * \sqrt{\left(\frac{F}{A}\right)}$$

where:
K=a constant determined by the geometry of the orifice;
F=spring force; and
A=syringe cross-sectional area.

Further, it should be noted that the pressure drop across an orifice is governed by inertial effects of the fluid; the viscosity of the fluid has little to no impact. As a result, an orifice minimizes the influence of the viscosity of the fluid on the rate of flow of the fluid. Under this circumstance, by using an orifice as a fluid flow restrictor, the Bernoulli effect predicts the same flow rate regardless of temperature of the fluid and regardless of which gadolinium compound is employed. Although in practice it is essentially impossible to entirely eliminate viscosity effects of the fluid, those effect are markedly reduced.

TABLE 1 provides the infusion rate, with respect to three MR contrast agents, for a variety of needles and flow restricting orifices when employed in an infusion device 12 substantially as illustrated in FIG. 5A where the spring 40 is a 6 pound-force spring and the syringe 24 is a 1 inch diameter, 50 cc syringe.

In those instances where the rate of flow of the fluid is dependent on the ambient temperature or the temperature of the contrast agent, consistent operation of the infusion device 12 may require either a temperature controlled operating environment or use of a fluid flow restrictor whose operational characteristics are essentially unaffected by the viscosity of the fluid (e.g., a precision orifice).

With reference to FIG. 5B, in one embodiment, the rate adjustment mechanism 50 is a manual type including a lever 50a by which the user may increase or decrease the force applied to the plunger 24a. The lever 50a engages the plunger 24a and spring 40 so that the resulting force applied to the plunger 24a is essentially determined by the sum of the force applied to the plunger 24a (i.e., by the lever 50a) and the spring force, F. By employing this configuration, the user may increase or decrease the rate of injection at a particular moment of the imaging sequence. For example, increasing the infusion rate at about 10 to about 40 seconds prior to the acquisition of image data corresponding to the center of the k-space would cause an elevated, substantially elevated or relatively high arterial gadolinium level to be maintained in the artery of interest during acquisition of image data corresponding to the center of k-space (typically it takes about 10–40 seconds for venous blood in the arm to circulate through the heart and lungs to reach the artery of interest). Such a technique may provide additional contrast enhancement of the image of the artery relative to veins and surrounding tissue.

It should be noted that the center of k-space may be characterized as 10% to 75% of the total k-space data which corresponds to the lowest spatial frequency information.

It should be further noted that a substantially elevated concentration of the contrast agent in the arterial blood may be described as a concentration which is greater than 2.9/seconds-relaxivity (of the contrast). As mentioned above, a substantially elevated rate of infusion provides a substantially elevated concentration of the contrast agent in the artery of interest.

The infusion device 12 of FIG. 5B further includes a flow rate indicator 52 to provide the operator an indication of a flow rate (injection rate) of the contrast agent to the patient. Here, the operator may visually or audibly observe the rate of flow of the contrast agent to thereby accurately control the rate of injection of the contrast agent into the patient; the operator may customize or modify the contrast injection rate.

The flow rate indicator may be implemented using an optical type sensor for sensing the linear motion of, for example, the plunger 24a, the spring 40, and/or the block and spring housing 30a, or the rotational motion of the roller bearings 30b. Such a mechanism permits an accurate measurement with little to no impact on the operation of the injection device 12, including the motion of the plunger 24a and the operation of the spring 40. That is, an optical type rate indicator has an advantage of not requiring physical contact with the contrast agent in the syringe 24 or spring 40.

It is noted, however, that a fluid flow or motion sensor may also be employed in the flow rate indicator 50. Such devices provide accurate information regarding the rate of flow of the contrast agent in the syringe 24 or in the tubing 34a.

As mentioned above, when the mechanical infusion device 12 is employed within the environment of the magnetic field, the materials used to fabricate the device 12 should be non-magnetic. That is, magnetic materials should be avoided when the device 12 is implemented in or near the magnetic field of the magnetic resonance imaging apparatus. In those instances, the spring 40 (FIGS. 5A and 5B) should be manufactured from non-magnetic materials, for example, eljaloy or inconel.

Figure 6A:
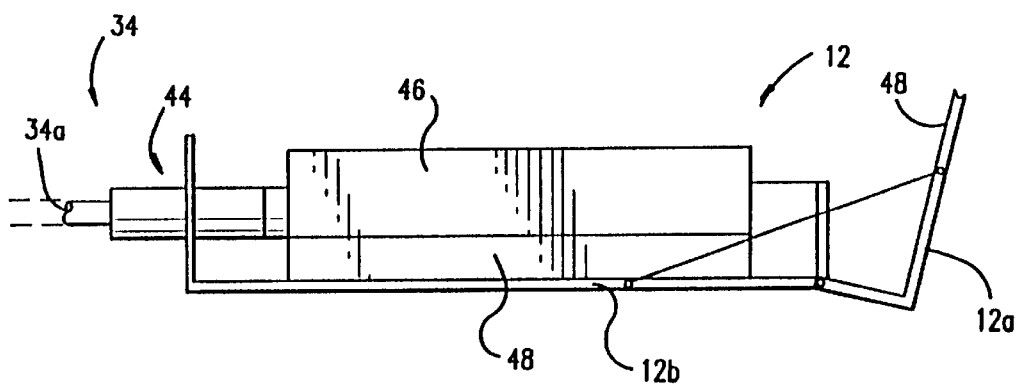
Figure 6B:
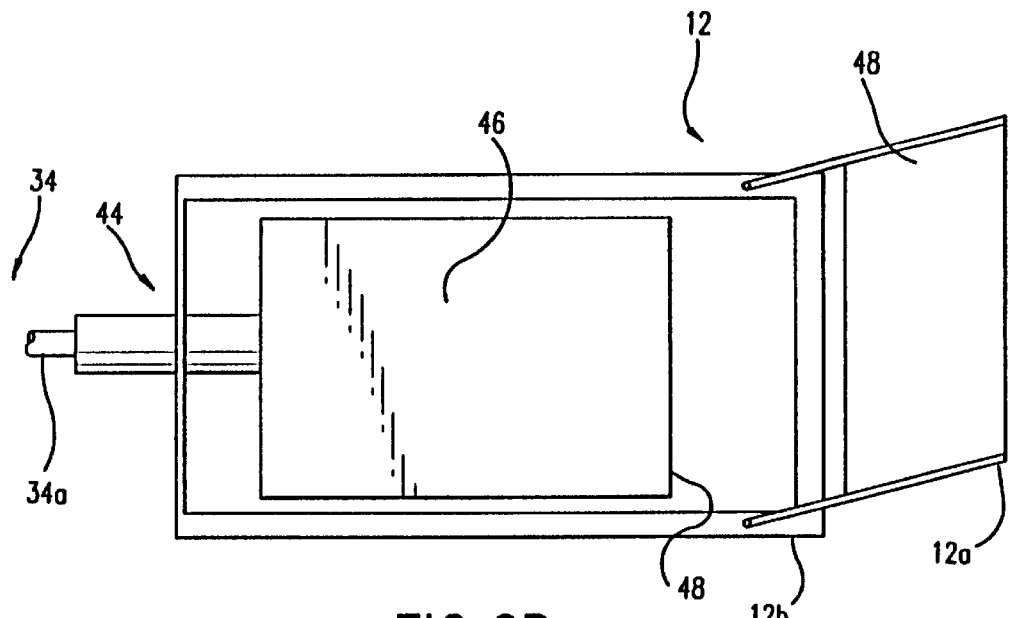
Figure 6C:
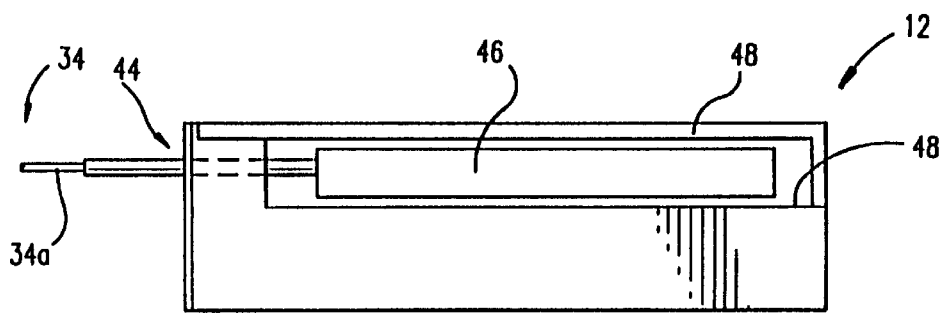

With reference to FIGS. 6A–C, the mechanical infusion device 12 may be implemented using a bag-cassette configuration. The bag 46 contains a contrast agent. Analogous to the syringe configuration of FIGS. 5A and 5B, the bag 46 may be placed into a cassette 48 which applies even pressure over the contact surface of the bag 46. In operation, the contrast agent then flows, similar to the syringe 24, from the bag, through the catheter 34 to the patient. As with the case with the syringe configuration, fluid flow control is provided by means of a fluid flow restrictor (i.e., the needle 34b) used in combination with a cassette 48 which provides the force.

It should be noted that the bag-cassette arrangement of FIGS. 6A–C may employ a saline drip apparatus 42 as well as a rate adjustment mechanism 50. As with the syringe configuration, the rate of injection may be increased or decreased using a manual, spring loaded, or electrical or pneumatic rate adjustment mechanism.

In some magnetic resonance suites, an opening exists in the wall dividing the magnet of the imaging apparatus and the control equipment (i.e., computer and other electronic devices). In these situations, standard infusion pumps (containing metal, magnetized material and electronic circuits) can be used from outside of the MR suite to implement the methods described herein.

In one preferred embodiment, a pump manufactured by Abbott, the Life Care 5000, may be implemented. The Life Care 5000 draws drugs (e.g., contrast agent) directly from a bottle and preloads it into a long length of tubing. The operating parameters of the Life Care 5000 may be preprogrammed to execute numerous infusion rates.

In another preferred embodiment, the injection rate for contrast is matched with the mapping of k-space so that a maximum or substantially elevated arterial gadolinium concentration correlates with acquisition of image data corresponding to the center of k-space. That is, the operating parameters of the pump may be pre-programmed to provide an injection rate for contrast agent which is matched with the mapping of k-space so that a maximum or substantially elevated rate of infusion occurs about 10–40 seconds prior to the collection of image data corresponding to the center of k-space.

The operating parameters of the pump may also be controlled by the detection system 110 (as described below). The timing of a maximum, elevated or substantially elevated rate of injection may be controlled by the detection system 110 in order to more accurately synchronize the collection of image data which is representative of the center of k-space to a maximum, elevated or substantially elevated concentration of contrast in the artery of interest. This embodiment is discussed in more detail below.

This type of configuration offers several advantages including: (1) the contrast agent (gadolinium) need not be removed from its shipping containers into an intermediate container, for example, a syringe; (2) the programmability of the pump allows variable injection rates providing for a maximum rate at the peak when the center of k-space is being mapped (which may be the most critical period during image acquisition); (3) operator control of the operating parameters. Moreover, the Life Care 5000 may be coupled to the detection system 110 to facilitate the mapping of k-space by the imaging system 16 with the arterial phase of contrast enhancement in the region of interest.

It should be noted that the Life Care 5000 Pump may not be ideally suited for implementing all of the techniques described herein. For example, such deficiencies include the rates of injection of the pump, the degree of programmability of the flow delivery characteristics of the pump, and allowing the pump to administer contrast from multiple containers which will permit multiple 20 cc vials to be used.

When implementing longer pulse sequences (greater than 2 minutes) or pulse sequences which collect image data representative of the center of k-space some time after initiation of image data collection, it is important that no contrast be administered prior to magnetic resonance scan since the contrast may leak into the background tissues and cause a degradation of the image. If some paramagnetic contrast or other magnetic resonance contrast has been administered prior to imaging, it may be useful to delay the arterial scan until this contrast has been excreted by the patient, in order to increase the probability of obtaining optimal images.

An exception to this requirement is when a small test dose of contrast or the like (sodium dehydrocholate, saccharin or indocyanine green) is used to determine the circulation time prior to performing the dynamic injection with imaging. By infusing a small test dose of a few milliliters and then imaging rapidly the region of interest, it is possible to determine the time interval between contrast infusion and contrast arrival in the artery. This time may then be used to guide timing for the image acquisition in that it may facilitate more accurate correlation between the injection of the contrast agent and the acquisition of the data representative of the center of k-space when the imaging system 16 collects such data in the middle of the scanning sequence. Thus, this time should roughly equal the time between the middle of the infusion and the moment of acquisition of the center of k-space for short infusions.

In those instances where the imaging apparatus employs pulse sequences having very short data acquisition periods the contrast agent may be injected before the initiation of collecting image data. Short pulse sequences may be characterized as those sequences for which the time required for contrast to circulate from injection site to the artery of interest becomes a significant fraction of the imaging time, for example, data acquisition periods of less than 2 minutes. Under this circumstance, injection of the contrast agent before acquisition of image data is necessary to allow circulation of the contrast agent in the patient and thereby correlate a maximum or substantially elevated arterial concentration with the collection of image data representing the center of k-space. Administering the contrast agent prior to the acquisition of image data would cause a relatively high arterial gadolinium level during the mapping of k-space. As discussed above, the relative timing between the administration of the contrast agent and the collection of image data representing the center of k-space should be adapted to account for the injection mechanism employed, the location of the artery of interest, the size of the artery of interest, and the physical condition of the patient. For example, the contrast may be administered about 10–40 seconds before collection of image data to account for venous blood in the arm to circulate through the heart and lungs to reach the artery of interest. Thus, the amount of time before acquisition of image data may depend on the configuration of the contrast delivery mechanism, the relative location of the artery of interest, the relative size of the artery of interest, and the condition of the patient, including the age of the patient. Employing these considerations in selecting and controlling the timing of the injection provide a more accurate alignment between the acquisition of data representative of the center of k-space and a period of maximum or substantially elevated contrast concentration in the artery of interest relative to adjacent veins.

When employing the conventional imaging sequence which maps k-space in the middle of the scan, in a preferred embodiment, a constant infusion should begin within a few seconds of initiation of the scan process. The contrast infusion should end about 20 or more seconds before the completion of the scan; this allows the intravenously injected contrast to circulate through the heart and into the arteries. A chaser of normal saline or other fluid may be used to insure injection of the entire dose of the paramagnetic contrast (e.g., gadolinium) and, in addition, to insure that there is sufficient venous return to propel the injected contrast to the heart. In a preferred embodiment, the contrast infusion rate is matched with the mapping of k-space so that the maximum arterial gadolinium concentration occurs during acquisition of the center of k-space. This may permit injecting over a shorter period of time to achieve either a higher injection rate or a lower contrast dose.

In one preferred embodiment, the magnetic resonance contrast agent is injected by the infusion device 12 in a bolus manner and the imaging sequence, implemented by the imaging system 16, collects data which is representative of the center of k-space at or near the beginning of the sequence. Under this circumstance, in order to correlate, on a repeatable basis, a maximum, elevated or substantially elevated arterial concentration of the contrast agent in the artery of interest with the collection of image data corresponding to the center of k-space, the detection system 110 monitors or measures the response from the region of interest to detect the arrival of the contrast agent in that region. Upon detecting the arrival of the contrast agent in the region of interest, the imaging system 16 may initiate collection of image data representative of the center of k-space. The center of k-space corresponds to the low spatial frequency data which dominates image contrast.

In a preferred embodiment, the period of a maximum or substantially elevated rate of infusion of the magnetic resonance contrast agent to the patient is adapted according to the size of the artery of interest in order to correlate with the period of the collection of image data corresponding to the center of k-space to the period of the arterial phase of contrast enhancement. In this regard, where the artery of interest is relatively large (e,g., the aorta), a period of a substantially elevated or maximum injection rate may overlap for a smaller fraction of the total image time than where the artery is relatively small (e g., renal). For example, when imaging larger arteries, the administration of the contrast agent may include a period of a substantially elevated or maximum rate of contrast which provides a substantially elevated or maximum arterial concentration for less than 50% of the period during which the system collects image data corresponding to the center of k-space; and preferably between 20% to 50%. Where the artery of interest is relatively small, it is preferable that a period of maximum or substantially elevated rate of injection provide a maximum or substantially elevated concentration of the contrast in the artery of interest for more than 50% of the period of mapping the center of k-space; and preferably between 50% to 85%.

Figure 7:
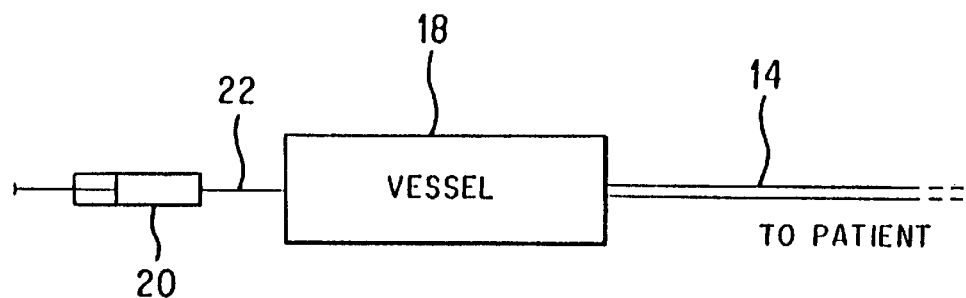
FIG. 7 is a block diagram representation of a manual injection configuration, according to the present invention.

With reference to FIG. 7, the infusion of the magnetic resonance contrast agent may be by way of manual means. In this embodiment, a syringe 20, having needle 22, is coupled to a vessel 18 containing the magnetic resonance contrast agent. The vessel is coupled to the patient using conventional techniques, for example, appropriately selected tubing 14 which permits fluid flow between the vessel and the patient, for example, an angiocatheter.

When injecting the contrast agent using a manual injector, i.e., injecting the magnetic resonance contrast agent by hand, during the magnetic resonance angiography sequences, in a preferred embodiment, the infusion "path" includes a fluid flow restrictor which adds resistance to the flow of gadolinium during administration into the body. It should be noted that a fluid flow restrictor may be, for example, a standard injection needle or small calibre angiocatheter. In FIG. 7, the fluid flow restrictor may be the needle 22 of syringe 20 and/or the angiocatheter 14. Use of small needles, short pieces of tubing of narrow calibre, an orifice, and/or small calibre angiocatheters may alleviate errors of injecting the contrast too rapidly and, as a result, depleting or running-out of contrast too early in the scan or improperly correlating a maximum or elevated rate of infusion with the mapping of k-space. In a preferred embodiment, the needle size may be 22 gauge or smaller diameter (higher than or equal to 22 gauge) depending upon the viscosity of the contrast agent for an infusion of 2–4 minutes. Angiocatheter of 20 gauge may be suitable for infusions of about 30 seconds.

It may be convenient to pre-load the entire dose of contrast into a vessel or length of tubing with luer lock or other appropriate connectors at each end of the tubing. It is then possible to use a single saline filled syringe to inject the contrast followed by a saline chaser without having to switch syringes or pumps. Saline is a preferred fluid to use as a chaser since it can be made isotonic with blood and is compatible with most intravenous fluids and pharmaceuticals that may already be flowing through a patient's IV line.

In a preferred embodiment, the contrast is infused slowly at the beginning and fastest near (about 10–50 seconds before) the middle of the acquisition. This type of injection pattern, based upon the fact that the contrast does somewhat contribute to venous and background tissue enhancement, avoids excessive contrast early in the acquisition.

In another preferred embodiment, the magnetic resonance is contrast agent is injected rapidly in a bolus manner and the imaging sequence implemented by the imaging system 16 collects image data which is representative of the center of k-space at or near the beginning of the sequence. Upon detecting the arrival of the contrast agent in the region of interest (by the operator or detection system 110), the imaging system 16 may initiate the imaging sequence and collection of image data representative of the center of k-space.

Another embodiment of a manual infusion means is illustrated in FIG. 13. In this embodiment, a syringe 20 is loaded with a magnetic resonance contrast agent. A 3-way stopcock 44 permits rapid contrast agent (e.g., gadolinium) injection without risk of retrograde flow. Another side port of the stopcock 44, further from the patient, accommodates an additional syringe 20' which may be employed as a rapid saline flush immediately following the contrast injection.

A drip chamber 42d allows the operator to observe that the tubing 14 is intravascular and working properly. In this regard, a bag of normal saline 42a, or other suitable fluid, is connected to the proximal end of the tubing 14 via a drip chamber 42d. The operator may observe the drip chamber 42d to determine whether the intravenous line is working properly. A roller clamp 42c may be employed to prevent too rapid saline flow into the patient.

It should be noted that a bag of saline 42a which is too large may be harmful to the patient should the entire volume of saline be administered to the patient; using a small bag of saline, accidental administration of the entire bag will not be harmful. Typically, a 250 cc bag of fluid is suitable for providing enough fluid to last for the entire exam and to avoid injury to the patient if there is accidental release of the entire quantity of the fluid into the circulation in a short span of time (e.g., in less than 15 minutes).

The dynamic infusion of contrast may be facilitated by using tubing 14 which reaches inside the magnet and which allows the operator infusing contrast to stand comfortably outside the magnet environment where it is possible to watch a clock and/or have access to control panels for the imaging system 16 to initiate the scan. With a sufficient length of tubing, the operator may comfortably use both hands to perform the infusion; generally one hand holds the syringe plunger and the other hand holds the syringe chamber.

In those embodiments where the operator is positioned outside the magnet environment, at least 4 to 6 feet of tubing may be required to reach outside the magnet environment. A side port for gadolinium infusion should be located about 4 to 7 feet away from the end of the tubing which is at the intravenous puncture site. A second side port a few inches further away is also useful to allow sufficient space for both gadolinium filled and saline filled syringes to be attached simultaneously. This allows the gadolinium infusion to be immediately followed with the saline flush without any delay for switching syringes. By placing one-way valves in the tubing upstream from each side port, the fluids (contrast agent and flush) are forced to flow in the correct direction without risk of retrograde flow in the tubing. One of the one-way valves should be between the two side ports so that the contrast agent may not "backup" into the other syringe used for flush. This is particularly important when the gadolinium is injected so rapidly that a high infusion pressure is required. The most proximal one-way valve could be replaced with a clamp or other mechanism to impede flow.

It may also be useful to have an extra port (a third port) positioned close to the distal end of the tubing where it attaches to the patient. This port can be used for treating any reaction that the patient might have to the contrast being infused. By having this third port close to the patient, it minimizes the distance that medicines must travel in order to reach the patient's circulation. It is anticipated that in the event of a contrast reaction, the patient would be immediately removed from the magnet so that this third port would be readily accessible.

Proximal and distal ends of the tubing should have standard medical type luer locking connectors. The distal end should have a male connector. It is useful if this distal end has a locking mechanism to prevent the tubing from becoming detached from the intravenous catheter during the increase pressure of fast infusions. A flow meter that provides feedback to the operator about the contrast infusion rate may be useful.

The inner diameter of the tubing 14 may be important. The tubing's inner diameter may be selected to strike a balance between a sufficient diameter to minimize flow resistance but not so large a diameter that there is a large dead space. Dead space is the volume of tubing between the IV site in the patient's arm and the point where the syringe 20 attaches to the tubing 14.

In one embodiment, a tubing inner diameter of about 0.08 inch strikes a good balance between the need to minimize resistance and the need to minimize dead space for tubing that is about 6 feet long with gadopentetate dimeglumine or gadodiamide as contrast agents. The tubing 14 may be made of plastic, rubber or any other suitable (non-magnetic) material. The tubing 14 should be pliable so that it can easily adjust or conform to the path of the intravenous site on the patient's arm to outside the magnet environment. In some situations it is also useful if the tubing assumes a natural coil configuration so that it will tend to stay wound up. This helps to avoid having the intravenous tubing becoming intertwined with other tubing or wires in the general vicinity of the magnet and imaging system 16.

Detection System

The detection system 110 detects the concentration of contrast agent in the region of interest; and, more particularly, detects the "arrival" of contrast in the region of interest as well as detects the concentration of contrast therein. In addition, the detection system 110 may be used to precisely synchronize the collection of a predetermined portion of image data (e.g., center of k-space) by the imaging system 16 with the arterial phase of contrast enhancement of the region of interest (artery and tissues in the region of interest).

The detection system 110, in conjunction with the imaging system 16, monitors and detects the relative concentration of the contrast agent in the region of interest by comparing the response of a region of interest before the administration of magnetic resonance contrast agent to the patient to the response of the region of interest during and/or after administration of the contrast agent. When a characteristic change in the response to the magnetic resonance pulse is measured by the detection system 110, the imaging system 16 begins collecting image data which is representative of the center of k-space.

In operation, prior to administration of contrast agent to the patient and before initiation of the imaging sequence, the detection system 110 initially measures the response from the region of interest to a series of pulses form the imaging system 16. Here, the detection system 110 acquires a response from the region of interest before administration of contrast agent. This response may be described as a base line or pre-contrast response.

After the base line or pre-contrast response is measured, the contrast agent may be administered to the patient. The detection system 110 may then measure the response from the region of interest to a series of magnetic resonance pulses from the imaging system 16. The detection system 110 or the operator may evaluate the response from the region of interest to determine a characteristic change in the response from the region of interest. This characteristic response may indicate the arrival of contrast in the region of interest or the onset of the arterial phase of contrast enhancement.

The subsequent operations of the detection system 110 depends somewhat on the parameters of injection rate of the injection system 12 and the data collection techniques and configuration of the imaging system 16. In this regard, in those instances where the injection of the contrast agent is of a bolus type (i.e., rapid injection rate), the characteristic change in the response to the magnetic resonance pulses may indicate that the region of interest is in or is "entering" the arterial phase of the magnetic resonance contrast enhancement. Under this circumstance, the detection system 110 instructs the imaging system 16 to initiate an imaging sequence. The imaging system 16, immediately or shortly thereafter, collects the predetermined image data of the imaging sequence (e.g., center of k-space).

It may be useful to have a short delay between detecting the arrival of contrast in the arteries of interest and beginning collecting data representative of the center of k-space. This delay may allow the contrast to reach all of the arteries throughout the entire imaging volume (region of interest).

In another embodiment, the imaging system 16 repeatedly collects data representative of the center of k-space before and during arrival of the contrast in the imaging volume. The remaining portions of k-space data (i.e., the periphery of k-space) may be collected either before or after contrast arrives in the imaging volume. It may then be possible to reconstruct a series of images showing the temporal pattern of contrast arriving in the imaging volume. In this embodiment, a detection system 110 may not be necessary.

In the alternative, however, the detection system 110 may detect when contrast has arrived in the imaging volume so that one or only a few more sets of data representative of the center of k-space need be acquired before switching to acquiring data representative of the remaining portion of k-space (i.e the periphery of k-space). In this embodiment, it may be useful if the data representative of the center of k-space corresponds to a small fraction of the total k-space data (i.e. 10–30%) so that it may be repeatedly collected in a short period of time for high temporal resolution of the vascular and tissue enhancement.

Where the predetermined image data is data which is representative of the center of k-space, the magnetic resonance imaging pulse sequence should be arranged such that the central portion of k-space data is collected in the beginning or near the beginning of the sequence. The periphery of k-space may be collected thereafter. Under this circumstance, the detection system 110 provides precise synchronization between the arterial phase of contrast enhancement and the collection of image data which is representative of the center of k-space.

Where the magnetic resonance pulse sequence collects data which is representative of the center of k-space in the middle of the scan (a conventional type scan), the detection system 110 may be employed to determine an "adjustment" of the infusion rate of the contrast agent by the infusion device 12 so that a period of maximum, elevated or substantially elevated concentration of contrast agent in the region of interest is correlated to the collection of image data which is representative of the center of k-space (i.e., mapping of k-space). As noted in the related applications, the time between contrast injection and a maximum or substantially elevated contrast concentration in the artery of interest may vary according to a number of factors including the location of the artery of interest, the size of the artery of interest, the physical condition of the patient, and the time delay due to the configuration of the infusion system 10. In this embodiment, the detection system 110 may be employed to automatically adjust the rate of infusion of the infusion device 12 so that the imaging sequence collects a sufficient amount of data which is representative of k-space during the arterial phase of the enhancement of the region of interest.

In this embodiment, the detection system 110 monitors the response of the region of interest to series of magnetic resonance detection pulses. When the detection system 110 determines that the contrast has "entered" the region of interest, the detection system 110 may adjust the rate of injection of the contrast agent to alter the timing of the arterial phase of contrast enhancement.

The detection system 110 may calculate an adjustment to the rate of infusion based on several factors including the circulation time delay of the contrast agent, the timing of the mapping of k-space, and the current and future rates of infusion. The detection system 110 may then increase or decrease the rate of injection by the infusion device 12 accordingly to provide sufficient or maximum overlap between the mapping of k-space and the arterial phase of contrast enhancement.

As mentioned above, the detection system 110 may detect the concentration of the contrast in the region of interest in a number of different ways including, for example, a change in the amplitude of the responsive radio frequency signal.

In one embodiment, the monitoring and evaluating operations of the detection system 110 and the imaging system 16 is initiated only when the contrast agent is expected in the region of interest. In this regard, the application of the detection pulses employed to detect/monitor the "arrival" of the contrast agent to the region of interest, may be delayed from the infusion of the contrast in an amount related to the time delay due to the infusion system 10 and the time-delay due to the time required for the contrast agent to circulate from the site of injection, through the body, and into the artery of interest. This will confine the use of the magnetic resonance imaging system 16 and detection system 110 to the period when the maximum, elevated or substantially elevated contrast concentration is anticipated.

Figure 12:
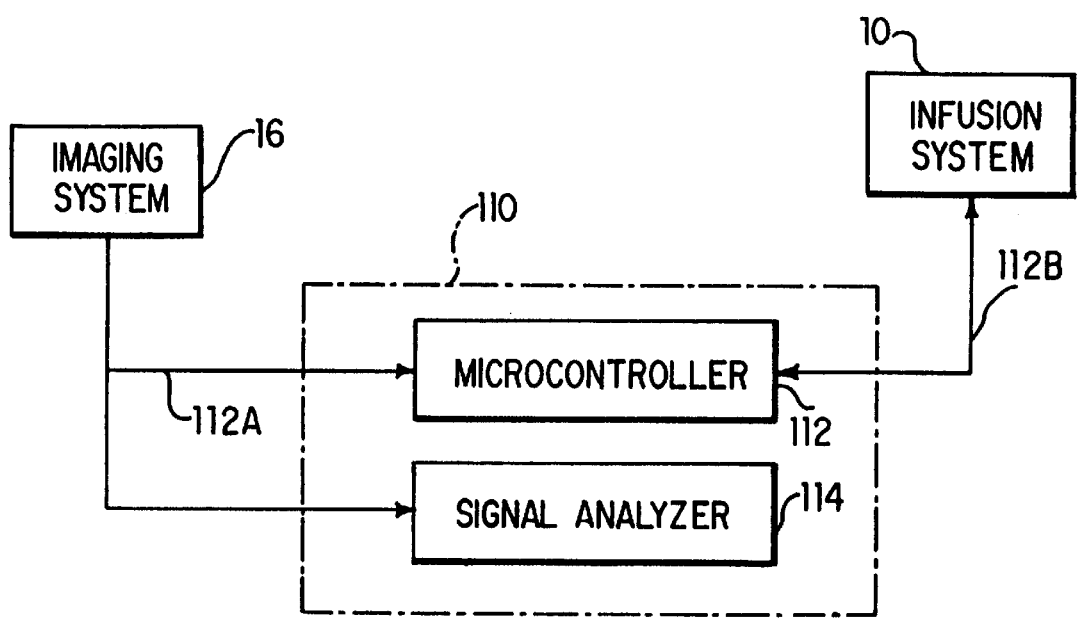
FIG. 12 is a detailed block diagram representation of one embodiment of the detection system in conjunction with the imaging system and the infusion system.

FIG. 12 illustrates the detection system 110 of the present invention. In this embodiment, the detection system 110 includes a microcontroller 112 and a signal analyzer 114 (e.g., an oscilloscope). The microcontroller 112 (which includes an adequate supply of memory) is programmed to calculate the base line or pre-contrast signal response from the region of interest prior to the administration of the contrast agent as well as the concentration of the contrast agent in the region of interest after administration of the contrast agent. The microcontroller 112 acquires an electrical representation of the signal response from the signal analyzer 114. In response, the microcontroller 112 calculates the base lines response and the contrast concentration in the region of interest.

In one embodiment, the detection system 110 controls the imaging system 16. In this regard, the detection system 110 instructs the imaging system 16 to initiate a predetermined imaging sequence at an appropriate time depending on detecting a characteristic change in the signal response from the region of interest, as described above. The microcontroller 112 couples to the imaging system 16 via electrical or optical coupling mechanism 112a.

In another embodiment, the microcontroller 112 includes an operator interface which allows the operator to observe the response measured by the signal analyzer 114. In this embodiment, the microcontroller 112 facilitates the operator's observation and analysis of response signals including assessing the concentration of contrast in the region of interest. The microcontroller 112 may include a visual and/or audible indicator to indicate the onset of the arterial phase of contrast enhancement or to indicate the concentration of contrast agent in the artery of interest. Such a configuration would facilitate synchronization between the collection of image data which is representative of the center of k-space with the arterial phase of contrast enhancement.

It should be noted that the operator may observe the signal measured by the signal analyzer 114 in addition to or in lieu of the operator interface of the microcontroller 112. Under this circumstance, the microcontroller 112 may be unnecessary.

In another embodiment, the microcontroller 112 controls the rate of infusion by the infusion system 10 (e.g., mechanical pump 12, Life Care 5000 and/or the size of the orifice of the fluid flow restrictor). Similar to the control of the imaging system 16, the microcontroller 112 (which is appropriately programmed) may adjust the rate of infusion to correlate the collection of image data which is representative of the center of k-space with a maximum, elevated, or substantially elevated concentration of contrast agent in the region of interest. The microcontroller 112 may adjust the rate of injection via controlling the infusion adjustment mechanism on the infusion device 12 (see, FIGS. 5A and 5B). The microcontroller couples to the infusion system 10 via electrical, optical, or pneumatic coupling mechanism 112b.

As mentioned above, the detection system 110 may compute an adjustment to the infusion parameters or sequence of infusion system 10 based on several factors including the circulation time delay, the relative timing of the mapping of k-space, and pre-programmed rate of infusion. The detection system 110 may then increase or decrease the rate of injection by the infusion device 12, via the infusion adjustment mechanism, to provide a period of arterial phase of contrast enhancement which extends during the collection of image data which is representative of the center of k-space.

Appendage Cushions

One important detail relates to the positioning of the arms during scanning. By placing appendage cushions 120a and 120b along either side of the patient's torso (see FIGS. 13A and 13B), the arms are elevated or lifted up in the air. This has several important effects. First, by lifting the arms, the intravenous site of contrast agent injection is elevated thereby creating a "down hill" path for the contrast agent which assists venous return. Under this circumstance, the contrast agent more rapidly enters the central veins to achieve a faster and more predictable circulation time. The circulation time is the time required for contrast agent (e.g., gadolinium) to circulate from the site of infusion through the body to the artery(ies) of interest.

An additional advantage of employing the appendage cushions 120a and 120b is that such an arrangement prevents the arms or other stuff from getting into the region along side the patient where it could result in aliasing (wrap-around artifact) when the imaging the torso with a coronally oriented volume.

In one embodiment, the cushions 120a and 120b may be made of foam or other material that has a low density of hydrogen nuclei. This is to ensure that the cushions 120a and 120b do not create much signal or noise during imaging. The length of the cushions 120a and 120b should be long enough to keep the arms up along the entire length of the torso. It may be useful in patients with wide hips and narrow torsos to make the cushion thinner in the region of the hips. Alternatively, the cushions may be short enough so that it comes down to the hips but does not overlap the hips.

In a preferred embodiment, the appendage cushions 120a and 120b are 8 cm thick of non-magnetic material, low density material. The appendage cushions 120a and 120b may be rectangular in shape and may be secured to the patient or the imaging apparatus prior to imaging using a non-magnetic strapping mechanism, for example, a velcro strap or similar material/mechanism. The surfaces 122a and 122b of the appendage cushions 120a and 120b may be shaped in a conformal nature to that of the patient's body. This shape provides for a more stable configuration so that there is little to no movement of the appendage cushions 120a and 120b relative to the patient.

Further, the upper surfaces 122a and 122b of the appendage cushions 120a and 120b may be sloped downward in the direction towards the patient. This shape allows the arms, when in a relaxed state, to rest in the corner of the torso and the upper surfaces of the appendage cushions 120a and 120b which minimizes movement of the arms of the patient during imaging.

Post-Processing

Post-processing of the scan data may be used. Maximum intensity projection (MIP) collapse images are useful for rapidly examining the entire arterial circulation within the region of interest. It may be useful to reformat and selectively collapse the data through the specific arteries of interest. Additional contrast may be obtained by digitally subtracting a pre-gadolinium acquisition from the dynamic gadolinium acquisition. Volume rendering and surface rendering may also be useful and is possible with these high contrast volume data sets.

Additional Sequences

After performing a dynamic contrast enhanced scan, it is possible to obtain additional MR angiogram images in which there is enhancement of both arteries and veins, as well as liver, spleen, kidney, and other organs. Phase contrast magnetic resonance angiography is also improved following the administration of magnetic resonance contrast. It may then be possible to combine a dynamically enhanced scan for visualization of primarily the arteries with one or more post-gadolinium (contrast agent) scans to resolve anatomic or physiological issues that may be important to a patient's condition.

Immediately below are examples of results obtained from use of preferred embodiments of the present invention. The parameters of the examples are detailed therein.

EXAMPLE 1

Contrast between peripheral arteries and veins in images obtained by imaging dynamically during the administration of gadopentetate dimeglumine was investigated in sixteen patients referred for aorta-iliac magnetic resonance arteriography. These included 9 males and 7 females with a mean age of 72 ranging from 67 to 83. The indications for the study included hypertension (6), abdominal aortic aneurysm (AAA, 6) claudication (4) and renal failure (9). Some patients had more than one indication. Parameters:

All imaging was performed on a 1.5 Tesla superconducting magnet (General Electric Medical Systems, Milwaukee, Wis.) using the body coil and version 4.7 or higher software. A 3D FT, coronal, spoiled, gradient echo volume was acquired centered on the mid-abdomen. The imaging parameters included: 12 cm volume with 60 partitions, 2 mm partition thickness, TR of 25 msec, a TE of 6.9 msec, a flip angle of 40°, first order flow compensation, 36 centimeters field of view, 256 by 192 matrix. The imaging time was 5 minutes and 10 seconds. Frequency was set superior to inferior so that phase artifact from diaphragmatic and cardiac motion would not superimpose on the abdominal aorta and IVC. When possible, phase artifact noise was minimized by excluding the heart and lungs entirely from the field of view. No saturation pulses were employed. The volume data were reformatted through vessels of interest and also displayed as maximum intensity projections. Gadopentetate Dimeglumine Injection:

After pre-scanning, venous access was obtained via a 22 gauge angiocatheter. A dynamic acquisition was then performed during hand injection of gadopentetate dimeglumine (Berlex Laboratories, Cedar Knoll, N.J.), 0.2 millimoles/kilogram. The injection was initiated within 5 seconds of initiating the image acquisition. The injection rate was constant (within the limitations of a hand injection) and timed to last until 10–20 seconds before completion of the scan. The injection included a 5 cc normal saline chaser to ensure injection of the entire gadopentetate dimeglumine dose. As a result, the gadopentetate dimeglumine ended approximately 30–40 seconds before completion of the scan and the saline chaser ended about 10–20 seconds before completion of the scan. In order to compare to the conventional, non-dynamic, gadolinium-enhanced MRA, a second, identical acquisition was then acquired without altering the imaging or prescan parameters.

Signal Measurements:

Signal intensity was measured in the abdominal aorta, IVC, iliac artery and vein, renal artery and vein, celiac trunk, SMA, portal vein, hepatic vein and background tissue (including fat, skeletal muscle, kidney, liver and spleen) for 7 regions of interest per measurement. As many of these measurements as possible were obtained from the central 20 partitions and all measurements were obtained from the central 40 partitions. Identical regions of interest were used to compare vessels on the dynamic and post-gadolinium images. The standard deviation of the aorta signal was recorded as noise. Differences in the aorta and IVC signal-to-noise ratio were evaluated for each patient as well as for the means of all patients with Students t-test. In addition, the significance of differences in the mean portal vein, hepatic vein, renal vein and iliac vein signal compared to the IVC were evaluated with Students t-test. The presence of aneurysms, occlusions and stenoses (>50%) was noted on the individual dynamic images and on maximum intensity projections and compared to findings at surgery or arteriography when available.

Results

All sixteen patients tolerated the imaging and gadopentetate dimeglumine well; there were no complications. FIGS. 8A–C illustrate the typical images obtained before, during and after injection of gadopentetate dimeglumine, respectively. Before the injection, the vessels were heavily saturated with only a few streaks of vessels visible at the edges of the 3D volume. Images obtained during injection showed enhancement of the arteries while the IVC remained indistinguishable from the background tissue. Aorta IVC signal intensity ratios, shown in TABLE 2, confirmed this preferential arterial enhancement in every patient studied. Images obtained after the injection was completed demonstrated comparable enhancement of both arteries and veins.

It should be noted that with dynamic imaging there is bright arterial as well as portal vein and splenic vein enhancement but no visible IVC or iliac vein enhancement and no in-plane saturation. Post gadopentetate dimeglumine images show comparable enhancement of both arteries and veins.

TABLE 3 provides the average signal intensity for all tissues studied for both the dynamic and post-injection sequences. With dynamic gadopentetate dimeglumine the average aorta signal-to-noise ratio was 10±0.9 compared to 5.1±1.4 in the IVC (p value≦0.0001), while post gadopentetate dimeglumine the aorta and IVC were nearly identical, 10±1.4 and 9.5±1.3 respectively. Although all veins were less bright than the aorta on the dynamic images compared to post gadopentetate dimeglumine images, there were variations among the veins analyzed. The iliac vein was the least enhanced, 4.7±1.6, while the portal vein was the brightest, 8.3±1.6 followed by the hepatic, 7.5±2.1, and renal, 6.2±1.8, veins; these differences were significant to the p<0.01 level compared to the mean IVC signal-to-noise ratio.

Angiographic and/or surgical correlation was available in 6 of the 16 patients. In the vascular segments for which definitive correlation was available, magnetic resonance arteriography correctly identified 2 occlusions (1 common iliac and 1 renal artery), 10 stenoses (4 renal artery, 2 iliac artery, 2 distal aorta, 1 inferior mesenteric artery and 1 celiac) and 6 aneurysms (3 aortic and 3 iliac artery). There was no evidence of arterial in-plane saturation in any patient. In one patient with a common iliac artery occlusion, there was no difficulty visualizing reconstituted flow distal to the occlusion.

TABLE 4 reveals an apparent trend for patients with a history of cardiac disease, claudication or aneurysms to have the greatest aorta/IVC signal intensity ratio. The sample size may have been too small to establish statistically significant correlations. Further, one patient with cardiac disease, aneurysmal disease and claudication had the highest aorta/IVC signal intensity ratio. These trends are opposite from time-of-flight imaging where cardiac disease and aneurysms are associated with image degradation.

EXAMPLE 2

In order to determine the optimal timing of contrast administration, two methods of dynamic administration, bolus and continuous infusion, were compared to non-dynamic injections and to conventional time-of-flight imaging.

Gadolinium enhanced magnetic resonance arteriography was performed in 52 patients referred for routine MRA of the abdominal aorta or branch vessels. Imaging was performed as described in Example 1. The total acquisition time was 5:08 minutes to cover approximately 36 cm of aorta and iliac artery in the superior to inferior dimension. In 20 of these patients, the dynamic gadolinium infusion imaging was performed with 28 partitions each 2 mm thick with a 256 by 256 matrix to reduce the scan time to 3:18 minutes.

After pre-scanning, venous access was obtained via a 22 gauge angiocatheter. A dynamic acquisition was then performed during hand injection of gadopentetate dimeglumine (Berlex Laboratories, Cedar Knoll, N.J.) 0.2 millimoles/Kg. In 12 patients, the injection was given as a bolus. The bolus was begun within 5 seconds of starting the acquisition and completed within the first 1 to 2 minutes of the 5 minute scan. In the other 40 patients, an injection of the same dose was carefully timed to be constant and continuous over the entire period of imaging beginning within 5 seconds of commencing the acquisition and ending 20 seconds before the end of the acquisition. In all patients, a 5 cc normal saline chaser was given to ensure injection of the entire gadopentetate dimeglumine dose.

For comparison purposes, 16 of these patients were imaged with an identical acquisition after the dynamic infusion without altering the imaging or prescan parameters. Also, for comparison, axial 2D and multiple overlapping 3D (MOTSA) time-of-flight images were acquired prior to the gadolinium injection. Inferior pre-saturation pulses were used with the time-of-flight sequences to suppress venous in-flow.

Signal intensity was measured in all patients in the aorta, IVC and background tissues (fat and skeletal muscle) for at least 3 regions of interest per measurement for all sequences. The signal's standard deviation within the aorta was recorded as noise.

Images obtained dynamically, during steady infusion of gadopentetate dimeglumine, showed sufficient arterial enhancement to clearly define the aorta and branch vessel anatomy while the IVC and iliac veins remained indistinguishable from the background tissues. The portal vein is visible but is not as bright as the aorta. Images obtained non-dynamically, after the injection was completed, or with a dynamic bolus injection demonstrated comparable enhancement of both arteries and veins.

Figure 9:
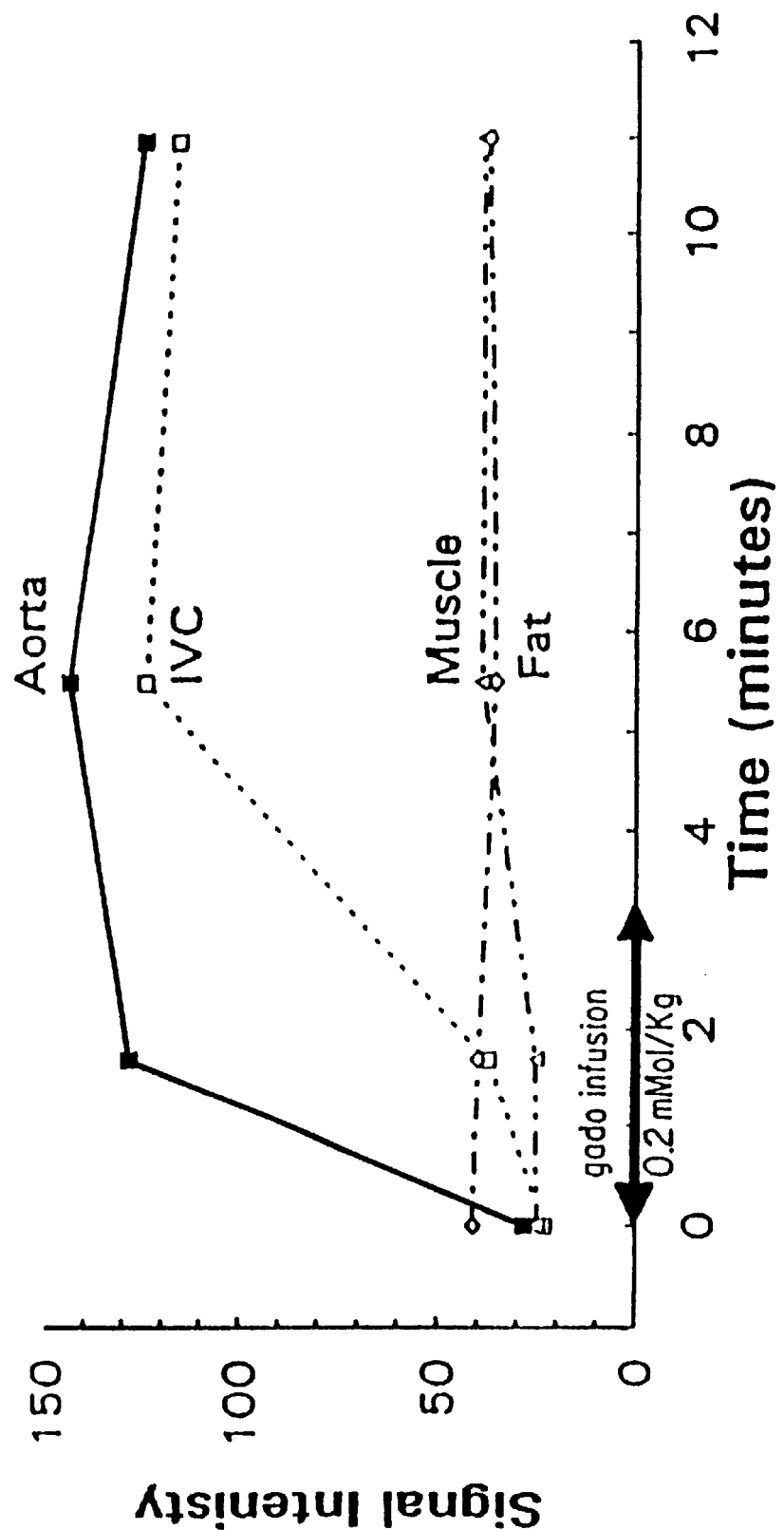
FIG. 9 illustrates region of interest analysis averaged for three patients who had pre-infusion, dynamic infusion, immediate post infusion and delayed 3D FT imaging. This figure shows that there is a short window, during contrast infusion, when the aorta signal intensity (solid squares) is higher than that of the IVC (open squares) and background tissues, fat (diamonds) and muscle (triangles)

The observation of significant, preferential arterial enhancement with a continuous dynamic contrast infusion was confirmed by region of interest analysis (see TABLE 5 and FIG. 9). The ratio of aorta to IVC signal intensity for the 5 minute infusion, 2.0±0.5, was significantly higher than for non-dynamic imaging 1.1±0.1 (p<0.001) or for the dynamic bolus 1.2±0.2 (p<0.001). Even better differentiation between the aorta and IVC was obtained by injecting the same dose of gadopentetate dimeglumine more quickly over a 3:18 minute acquisition. Although this aorta-to-IVC signal intensity ratio was not as favorable as for 2D time-of-flight or MOTSA imaging, it was adequate in all cases for clearly distinguishing the aorta and abdominal aorta branch vessels from the IVC and iliac veins.

Dynamic contrast enhanced 3D imaging had no saturation, pulsatility or misregistration artifacts. Even in aneurysms, which tend to have stagnant and/or turbulent flow, there was no loss of signal. By comparison, every 2D time-of-flight study had pulsatility artifacts and some had misregistration and/or in-plane saturation artifacts. The MOTSA images had no pulsatility or misregistration artifacts but every MOTSA study showed some degree of arterial saturation and they were particularly degraded in aneurysmal segments.

Administering gadopentetate dimeglumine dynamically as a steady, continuous, infusion for the entire period of a 3D FT acquisition, at a dose of 0.2 millimoles/Kg, gives sufficient preferential arterial enhancement to visualize arteries distinctly from veins and background tissues regardless of the magnitude or direction of flow. The importance of injecting dynamically and continuously during the entire scan is illustrated by the absence of significant preferential enhancement when the contrast is administered non-dynamically or as a dynamic bolus. Images obtained at a lower dose, 0.1 millimole/Kg, were not useful.

Since dynamic gadolinium enhanced MPA does not depend upon the in-flow of unsaturated spins, it eliminates some of the saturation problems that complicate routine time-of-flight imaging. The imaging volume can be oriented in any plane for optimal coverage of the vessels of interest without concern for saturation. In these patients, in-plane, coronal imaging of the aorta-iliac system reduced the image acquisition time by 5 to 20 fold over 2D time-of-flight and MOTSA imaging and had superior resolution and superior aorta signal-to-noise ratios.

A 3D FT acquisition was used in this example partly because of its intrinsically high spatial resolution and high signal-to-noise and also because its main limitation, arterial saturation, is eliminated by the gadolinium. The TE was chosen to be as short as possible at a value where fat and water protons are out of phase. A short TE helps to minimize motion related phase artifacts. Having fat and water out of phase provides an element of fat suppression which improves artery-to-background contrast since fat is the brightest background tissue.

EXAMPLE 3

MRA image data for a patient presenting with an abdominal aortic aneurysm was acquired as described in Example 1. MRA images are shown in FIGS. 10A and 10B.

Figure 10A:
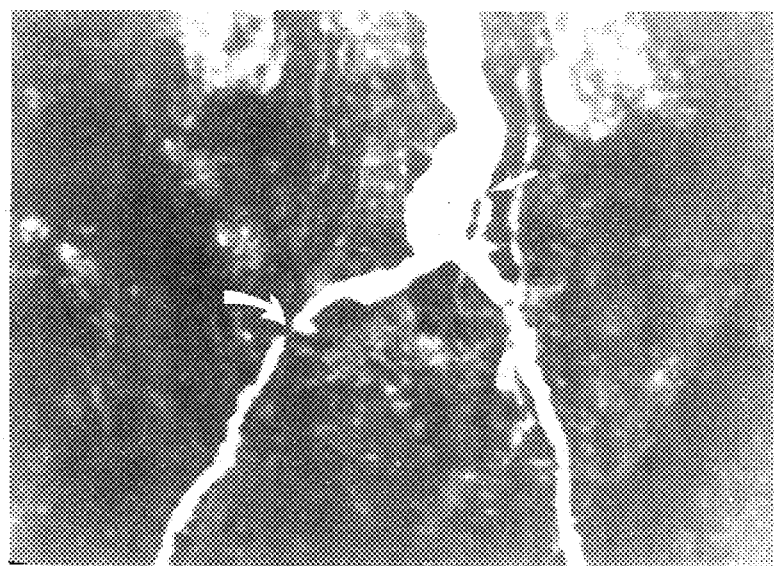
FIG. 10A is an illustrative example of a magnetic resonance image of a patient with an abdominal aortic aneurysm. The magnetic resonance angiography ("MRA") depicts the aneurysmal aorta and aneurysmal common iliac arteries as well as severe stenoses of the right external iliac (curved arrow) and inferior mesenteric (straight arrow) arteries and a mild stenosis of the left common iliac artery.
Figure 10B:
FIG. 10B illustrates a digital subtraction angiogram of the aneurysmal aorta and aneurysmal common iliac arteries as well as severe stenoses of the right external iliac (curved arrow) and inferior mesenteric (straight arrow) arteries and a mild stenosis of the left common iliac artery of FIG. 10A.

The MRA of FIG. 10A depicts the aneurysmal aorta and aneurysmal common iliac arteries as well as severe stenoses of the right external iliac (curved arrow) and inferior mesenteric (straight arrow) arteries and a mild stenosis of the left common iliac artery. The internal iliac arteries are excluded because of their posterior course. FIG. 10B illustrates a digital subtraction angiogram which confirms the findings in FIG. 10A as discussed immediately above.

EXAMPLE 4

A pump (as illustrated in FIG. 5A) was loaded with a 50 cc syringe containing 42 cc of gadodiamide. A 23 gauge butterfly was attached to the end of the syringe with its standard luer-lock connector and plugged into a side port of the patient's intravenous (IV) line within a few feet of the IV skin entry site. The pump was located approximately 15 cm or more away from the imaged volume.

Usually the IV site was in the forearm or antecubital fossa. A plastic Kelly clamp on the butterfly tubing prevented premature gadolinium infusion. The gadolinium infusion was begun simultaneously with beginning the image acquisition by releasing the clamp on the butterfly tubing. This combination of 6 pounds spring force and a ⅝ inch, 23 gauge butterfly needle gave an infusion rate of 18 cc/minute which was slightly reduced by the additional resistance of the IV tubing and angiocatheter. For the 42 cc volume of gadolinium, the calculated infusion time was 2:20 minutes. This was shortened by manually increasing the rate of injection during the middle of the acquisition such that the maximum arterial concentration occurred during acquisition of the center of k-space.

The pump infusion finished with one minute of scan time remaining. Residual gadolinium within the IV tubing (about 4 cc) was flushed through with saline to ensure delivery of the entire dose.

The procedure of EXAMPLE 4 produced excellent quality MRA images of arteries without the confounding effects of excessive venous enhancement.

EXAMPLE 5

By way of overview, anatomic data defined by magnetic resonance imaging, including abdominal aortic aneurysm size and character as well as the status of the celiac, mesenteric, renal and iliac arteries, were examined in 43 patients. Five magnetic resonance sequences used in examining these patients. The five magnetic resonance sequences were obtained in about an hour-long exam optimized for aortoiliac, splanchnic and renal artery imaging at 1.5 Tesla in a body coil. Four of the sequences were performed during or following infusion of gadolinium to improve image quality.

Imaging was performed on a 1.5 Tesla Magnet (GE Medical Systems, Signa, Milwaukee, Wis.) using the body coil. The imaging sequences included Sagittal T1 (9:36 minutes), Coronal 3D spoiled gradient echo during infusion of 42 or 63 ml gadolinium chelate (3:20 minutes), Sagittal 2D time-of-flight (4 minutes), Axial 2D time-of-flight (10 minutes), and Axial 3D phase contrast (13:07 minutes) images. Each sequence was performed using the GE Signa Magnet, 1.5 Tesla with 5.3 software. The imaging parameters, details regarding the gadolinium infusion rate and timing, and methods of image reconstruction are described in more detail below.

Magnetic resonance images were independently analyzed by two vascular radiologists blinded to the findings at angiography, surgery, and computed tomography. Any disagreements in interpretation were resolved by consensus. Aneurysms were classified as suprarenal (aneurysmal above the renal arteries), pararenal (aneurysm at level of renal arteries but not higher), juxtarenal (origin of aneurysm at or within 1 cm below renal arteries) or infrarenal (origin of aneurysm more than 1 cm below renal arteries). (See TABLE 6). The distal extent was defined as the first point inferior to the aneurysm that was near-normal caliber. The maximum aneurysm diameter was measured electronically on the MR computer monitor from its outer-to-outer wall margins. Thrombus, when present, was noted. The celiac, proximal superior mesenteric, renal, common iliac, external iliac, and internal iliac arteries were graded as normal, mildly diseased (less than 50%), moderately stenotic (50–75%), severely stenotic (greater than 75%) or occluded.

Magnetic resonance images were also evaluated for evidence of aortic dissection, inflammatory changes and aortic rupture. Aortic dissection may be defined as an aorta having an intimal flap or medial separation. Inflammatory aneurysm may be defined as having surrounding enhancing tissue. Ruptured aneurysm may be defined as having an aortic mural defect and a retroperitoneal collection with magnetic resonance features of hemorrhage.

The imaging parameter details are described below in a form compatible with the GE Signa Magnet, 1.5 Tesla with 5.3 software. Those parameters, however, may be converted or extrapolated for use with other imaging systems; and, as a result, they are exemplary in nature.

An initial sagittal T1-weighted spin echo localizer was landmarked just below the xyphoid and obtained using the following parameters: TR=333 msec, TE=25 msec, bandwidth=16 kHz, slice thickness=8 mm (performed as a triple interleave with no gap), respiratory compensation, matrix=256 by 128 pixels with frequency encoding superior to inferior, a 40–48 cm field of view and 2 NEX. Image acquisition time was 9:35 minutes.

A first gadolinium-enhanced acquisition was a coronal 3D spoiled gradient echo sequence centered on the abdominal aorta and obtained with the following parameters: TR=24 msec, TE=6.9 msec, flip angle=40 degrees, bandwidth=16 kHz, 28 slices with 2.5 to 2.8 mm slice thickness, matrix=256 by 256 pixels, frequency encoding superior to inferior, first order gradient moment nulling (flow compensation), field-of-view=36 cm, 1 NEX. No saturation pulses were employed; the total image acquisition time was 3:20 minutes.

The coronal volume was positioned with the top edge at the diaphragm just below the heart and the front edge anterior to the pre-aortic left renal vein where it passed under the superior mesenteric artery and anterior to the common femoral arteries at the level of the femoral heads. If the posterior edge of the volume did not reach back into the renal parenchyma bilaterally, the slices were made thicker up to a maximum thickness of 2.8 mm. In most cases, this 28 slice coronal volume was too thin to image the entire aneurysm; accordingly the anterior margin of the aneurysm was deliberately excluded on this sequence.

Gadolinium was infused during the acquisition in order to preferentially enhance arteries more than veins. The same volume, 42 ml (two vials, 21 mMol), Gadodiamide (Omniscan; Sanofi Winthrop Pharmaceuticals, New York, N.Y.), Gadoteridol (ProHance; Squibb Diagnostics, Princeton, N.J.) or Gadopentetate Dimeglumine (Magnevist; Berlex Laboratories, Wayne, N.J.) was used in every patient under 95 Kg (210 pounds). Patients weighing greater than 95 Kg were given three vials (63 ml) of gadolinium. The gadolinium infusion was begun simultaneously with image acquisition using an MR compatible infusion pump (Redington Medical Technologies, Inc. East Walpole, Mass.) The infusion was completed 60 seconds prior to scan termination including a 10 to 20 ml saline flush. This saline flush was given to ensure delivery of the entire dose of contrast. Special care was taken to maintain a high infusion rate during the middle of the acquisition when the center of k-space was acquired.

Immediately following the dynamic gadolinium acquisition, 6 to 8 contiguous, sagittal 2D time-of-flight, spoiled, gradient echo images were acquired, centered on the visceral arteries with the following parameters: TR=33, TE=minimum (7 msec), flip angle=45 degrees, bandwidth=16 kHz, slice thickness=6 cm, first order gradient moment nulling (flow compensation), matrix=256 by 192, frequency encoding superior-to-inferior, 36 cm field-of-view, 1 NEX. Each sagittal image was obtained during suspended respiration (7 seconds per breath hold). Immediately following these sagittal images, axial 2D time-of-flight gradient echo images were obtained in a similar fashion with the following parameters: TR=22 msec, TE=minimum full (12 msec), flip angle=60 degrees, bandwidth=16 kHz, slice thickness=8 mm with a 5 mm interslice gap, matrix=256 by 256, 28 to 32 cm field-of-view, first order gradient moment nulling (flow compensation), and no phase wrap. The axial images covered from above the celiac trunk to below the AAA. If the iliac arteries were aneurysmal, the axial 2D time-of-flight images were extended down into the pelvis. The acquisition was performed either with 2 averages (NEX) and suspended respiration or with 4 averages and phase reordering with respiration (respiratory compensation).

Following the time-of-flight images (sagittal and axial 2D time-of-flight images), an axial 3D phase contrast volume was acquired centered on the renal arteries with the following parameters: TR=24 msec, TE=7.7 msec, flip angle=45 degrees, bandwidth=16 kHz, field-of-view=32 cm, 28 slices with 2.5 mm slice thickness, flow compensation, no phase wrap, matrix=256 by 128, frequency encoding right-left, 32 cm field-of-view, 2 NEX with velocity encoding in all directions at 30 cm/sec. The image acquisition time was 13:07 minutes. Images were reconstructed with the phase difference method illustrating maximum velocity in all flow directions as well as right-to-left flow to evaluate the retrocaval course of the right renal artery. In patients suspected of having very slow renal artery flow, such as patients with a serum creatinine greater than 3 mg/dl, the velocity encoding was reduced to 20 cm/sec.

Images were reconstructed by a vascular radiologist using a computer workstation (GE Medical Systems, Milwaukee, Wis.). Subvolume maximum intensity projections and single voxel thick reformations were made through the origins of each of the major aortic branch vessels. The subvolume maximum intensity projections were made by reviewing the raw data images to identify the minimum number of images required to demonstrate the renal arteries and then collapsing these into a single coronal image. This was similarly performed for the aorto-iliac system. A sagittal subvolume maximum intensity projection was performed centered on the celiac and superior mesenteric arteries for both the dynamic gadolinium-enhanced coronal sequence and for the sagittal 2D time-of-flight sequence.

EXAMPLE 6

Twenty-five patients were imaged with a shortened 3D spoiled gradient echo acquisition that could be performed during suspension of respiration. To shorten the acquisition time to under 1 minute, the TR was reduced to 14 msec and the TE was reduced to 2.6 msec. A 28 slice 3D volume with a 256 by 128 matrix required a 58 second breath-hold and a 12 slice volume required a 29 second breath-hold.

Gadolinium was infused intravenously as a 30 second bolus beginning approximately 40 to 50 seconds before the middle of the image acquisition. In this way, the arterial gadolinium concentration was expected to be maximum during the middle of the acquisition when data representative of the center of k-space was acquired.

It should be noted that for short scans (i.e., less than 1 to 2 minutes) one manner of calculating a scan time delay (i.e., a delay between the beginning of imaging and the beginning of infusion) more accurately is to employ the following relationship:

Scan Time Delay =
    Estimated circulation time + (infusion time/2) − (imaging time/2)

The estimated circulation time is the time required for contrast to travel from the site of injection/infusion to the artery of interest; the infusion time is the time duration of the contrast infusion; and the imaging time is the time duration of the image acquisition. The relationship defined above assumes that the data representative of the center of k-space is acquired in the middle of the image acquisition. In those instances where data corresponding to the center of k-space is collected at a time other than during the middle of the acquisition, the relationship may be adjusted accordingly.

In all patients who were able to cooperate with breath-holding, the renal arteries were well seen all the way to the renal hilum. In two patients who could not cooperate with breath-holding there was degradation (blurring) of the distal renal artery making it more difficult to evaluate.

EXAMPLE 7

Patients: Sixty-three patients underwent magnetic resonance angiography ("MRA") of the abdominal aorta including renal and mesenteric arteries using dynamic gadolinium enhancement during breath holding. The patients included 28 males and 35 females, ranging in age from 22 to 87 years. Primary indications for imaging included suspected renovascular hypertension (n=25), suspected mesenteric ischemia (n=13), abdominal aortic aneurysm (n=5), renal transplant donor (n=5), peripheral vascular disease (n=4), renal mass (n=2), renal failure (n=2), aortitis (n=1) and to evaluate vascular anatomy post aortic reconstruction (n=6). Nine patients had renal insufficiency with serum creatinines ranging from 1.6 to 10.4 mg/dl (mean=3.2 mg/dl).

Imaging Technique: All patients were imaged in a 1.5 Tesla super conducting magnet (Signa with 5.3 or 5.4 operating system software, General Electric Medical Systems, Milwaukee, Wis.) using the body coil. Three sequences were performed as follows:

(1) An initial sagittal Ti-weighted spin echo localizer was obtained centered just below the xyphoid using the following parameters: TR=385 msec, TE=17 msec, bandwidth=16 kHz, slice thickness=8 mm (performed as an interleave with no gap), respiratory compensation, matrix=256×256 pixels with frequency encoding superior to inferior, a 40–48 cm field of view, and two averages (NEX). Image acquisition time was 7 minutes 11 seconds.

(2) The initial sagittal Ti-weighted spin echo localizer sequence was followed by a coronal 2D time-of-flight spoiled gradient echo sequence with the following parameters: TR=20 msec, TE=6.9 msec, flip angle=30 degrees, bandwidth=16 kHz, field of view=32 cm, slice thickness=2.9 mm and first order gradient moment nulling. With a 256×128 matrix and two averages it was possible to acquire three sequential images in a 16 second breath hold. Images were obtained from just anterior to the left renal vein back to the renal hila, with a total of 14 to 24 images.

(3) A gadolinium-enhanced, 3D, spoiled gradient echo MRA sequence was performed during breath holding following the coronal 2D time-of-flight spoiled gradient echo sequence. For examinations focusing on the renal arteries (48 patients), this sequence was performed in the coronal plane graphically prescribed on a midline sagittal T1-weighted image (sequence #1). The coronal 2D time-of-flight images of sequence #2 were used as a guide for determining the anterior and posterior extent required to cover the renal arteries. For exams focusing on the celiac trunk and superior mesenteric artery (15 patients), this sequence was performed in the sagittal plane graphically prescribed on a coronal 2D time-of-flight image of sequence #2.

Breath Holding: Since most patients can suspend breathing for a maximum of 30 to 60 seconds, the parameters were adjusted to keep the acquisition time to under 1 minute. The TR was reduced to 14.1 msec, and the TE was reduced to 2.6 msec by using an asymmetric echo and eliminating the gradient moment nulling (flow compensation). With a 256× 128 matrix, it was possible to acquire a 12 slice volume in 29 seconds or a 28 slice volume in 58 seconds using a 16 kHz bandwidth. The actual number of slices was 16 or 32 but two slices at each end of the volume were discarded due to aliasing from phase encoding in the slice select direction. Frequency encoding was superior-to-inferior.

Initially, it was thought that most patients would have difficulty suspending breathing for longer than 30 seconds. Accordingly, the first patients studied were imaged with the 12 slice 3D volume and a 256×128 matrix that required only 29 seconds. The slice thickness had to be at least 3–3.5 mm in order to cover renal arteries from their origins to the renal hila or to adequately cover the celiac and SMA.

When it became apparent that many patients could suspend respiration for longer than 29 seconds, the image acquisition time was increased to 43 seconds (12 slices with a 256×192 matrix) and subsequently to 58 seconds (28 slices with a 256×128 matrix). For the 28 slice acquisitions, the slice thickness could be reduced to 2 mm except for the patients with abdominal aortic aneurysms who required 2.5 to 3 mm thick slices. A total of seven patients (eight exams) were imaged in 29 seconds, 11 (12 exams) were imaged in 43 seconds and 45 (46 exams) were imaged in 58 seconds.

All patients were instructed to take four deep breaths in rapid succession (hyperventilation) prior to breath holding. Oxygen was administered at a rate of 2 to 4 L/min by nasal canulae to patients who were likely to have difficulty suspending respiration. These patients were also given the option to take a single quick breath toward the end of the scan if breath holding became intolerable.

Appendage Cushions: To maintain high spatial resolution with the reduced number of phase encoding steps, the field of view was reduced to 26–32 cm. For coronal acquisitions, this small field of view lead to aliasing in the right-left direction. Appendage cushions resolved the difficulties presented by aliasing. The appendage cushions (about 8 cm thick of non-magnetic, low density, "spongy" material, e.g., foam) were positioned along each side of the torso to elevate the arms out of the image plane (FIG. 13). In addition to reducing the aliasing presented by a small field of view, the appendage cushions elevated the arms which enhanced the venous return for rapid clearing of gadolinium from veins.

Flip Angle Selection: To determine a suitable flip angle, the arterial blood signal intensity was calculated for a range of flip angles and T1 relaxation times. The calculated arterial blood T1 is 28 msec for a dynamic infusion of 40 ml gadopentetate dimeglumine over 30 seconds (40 mMol/min) into a cardiac output of 5 liters/min (8 mMolar). However, the actual arterial blood T1 occurring during the center of k-space is likely to be substantially longer than 28 msec due to the imperfect timing of the gadolinium bolus in relation to the mapping of k-space. Additional factors contributing to a longer T1 include stagnation of gadolinium in the veins beyond 30 seconds and the failure to complete the injection and flush in 30 seconds. Based on these calculations and considerations, a flip angle of 45 degrees was selected to maximize arterial contrast for an estimated arterial blood T1 of approximately 50 msec.

Timing of the Gadolinium Bolus for Breath Hold Gd MRA: All patients received 42 ml (two vials) of gadolinium contrast (gadodiamide, Nycomed, New York, N.Y.; gadoteridol, Bracco, Princeton, N.J.; or gadopentetate dimeglumine Berlex Laboratories, Wayne, N.J.) regardless of weight although the dose per weight was recorded. In preparation for the injection, the intravenous line was filled with gadolinium using 5–8 ml depending on the length of IV tubing. This process of initially filling the intravenous tubing provided a sense of flow resistance and thus aided gauging how much force was required for the injection. The gadolinium was injected by hand over 25 to 30 seconds and immediately followed with 20–50 ml normal saline to complete delivery of the entire gadolinium dose and to flush the veins of gadolinium. To help minimize any delay in performing the saline flush, intravenous tubing with two side ports was used, one for gadolinium and one for the saline flush (FIG. 13). When gadopentetate dimeglumine was used, its viscosity was reduced by placing it in a 37° C. incubator 2 to 3 hours prior to injection. This lowered its viscosity to a level comparable to gadodiamide and gadoteridol, making it possible to rapidly infuse through a 20 or 22 gauge angiocatheter.

Since the 3D spoiled gradient echo sequences on Signa systems fill in k-space linearly, from bottom to top, the central half of k-space was acquired during the middle half of the acquisition. It was the central portion of k-space that had the low spatial frequency information which dominated image contrast. In order to make arteries bright, the gadolinium bolus was timed for the arterial phase to occur during acquisition of this central portion of k-space.

The time required for the intravenously administered gadolinium to reach the abdominal aorta has substantial variation, which may range from 10 to 50 seconds for injections into an antecubital vein. This circulation time is generally longer in older patients and in patients with poor cardiac output. It is shorter in young, hypertensive individuals. For each patient, the circulation time (peak) was estimated based on age and clinical status. As indicated in Example 6, a "scan delay" between beginning the gadolinium infusion and beginning the 3D acquisition may be calculated from the following estimate of the circulation time of the contrast agent:

Scan Delay =
 Estimated Circulation Time + (Infusion Time/2) − (Imaging Time/2)

Using this approach, the middle of the 30 second infusion was expected to reach the arteries during the midpoint of the acquisition, thereby providing maximum arterial gadolinium concentration in the region of interest during acquisition of at least the central half of k-space.

For example, a 25–55 year old hypertensive patient with an estimated circulation time of about 15 seconds who could suspend respiration for 58 seconds would have a delay between beginning the infusion and beginning scanning of about 1 second. Older patients with cardiac disease or an aortic aneurysm with an estimated circulation time of 25 to 35 seconds would have a delay between beginning the infusion and beginning scanning of 10 to 20 seconds for the 58 second breath hold or 25 to 35 seconds for the 29 second breath hold. If the intravenous line was in the hand or distal forearm, the scan delay was made a few seconds longer and a larger saline flush was used.

Image Reconstruction: Images were reconstructed by a vascular radiologist using a computer workstation (General Electric Medical Systems, Milwaukee, Wis.). Subvolume maximum intensity projections (MIPs) and single voxel thick reformations were made through the origins of each renal artery, the celiac trunk and the superior mesenteric artery. Reformations were performed in flat 2D planes and occasionally in curved planes as well. The subvolume MIPs were made by reviewing the raw data images to identify the minimum number of images required to demonstrate the renal arteries and then collapsing these into a single coronal image. MIPs were also made in axial, sagittal, and oblique planes by orienting the plane of reformation for optimal alignment to the artery-of-interest and then increasing the slab thickness to encompass the entire artery.

Image Analysis: In order to evaluate image quality, the signal-to-noise ratio (SNR) and artery-to-adjacent tissue contrast-to-noise ratio (CNR) were measured in the aorta in every patient and in the proximal and distal renal artery in patients imaged in the coronal plane. These measurements were also obtained in 104 consecutive patients imaged with the previously described coronal 3D technique performed without breath holding. The standard measurement of the intrinsic image noise made from a region outside the patient was not possible because of the small field of view. Assuming that the arterial blood signal should be uniform over the vascular region of interest, any variation in arterial blood signal was considered to represent a combination of both the intrinsic image noise and the additional image noise from respiratory and other motion artifacts. Accordingly, the standard deviation of the arterial blood signal was considered "total noise" in that vascular segment for purposes of calculating the SNR. The signal-to-total-noise ratio is denoted as SNR* to distinguish it from the more conventional SNR measurement. Similarly, the contrast-to-total-noise ratio is denoted as CNR*. Degradation of images from blurring of the abdominal organs was also noted.

MRA was correlated with angiography by comparing the reports generated prospectively for each of the MR studies with the conventional angiography reports. All MRA exams were interpreted by a single vascular radiologist without knowledge of the angiography reports. Renal, celiac and mesenteric arteries were graded in these reports as normal, mildly stenotic (<50% stenosis), moderately stenotic (50–75% stenosis), severely stenotic (>75% stenosis) occluded or not visualized. The MRA was considered to "agree" with conventional angiography if the celiac, SMA and renal arteries were graded in MR reports the same as in angiography reports. The number of accessory renal arteries and renal artery branch vessels (including both hilar and prehilar branches) visualized by MRA for each kidney were also determined.

Statistical Analysis: The differences in SNR* and CNR* measurements and in the mean number of branch vessels seen between the free breathing and breath held techniques were compared using Student's t-test. Differences in the proportions of exams with blurring and the proportions of kidneys for which renal artery branches were seen between the free breathing and breath-held techniques were compared using the Chi square test.

Results: In all patients, the abdominal aorta and the origins of the celiac, superior mesenteric artery and renal arteries were visualized on breath held 3D gadolinium MRA.

Image Quality: There was 25–50% greater SNR* and 60–120% greater CNR* with breath holding compared to free breathing (p<0.01) as shown in Table 7. The breath holding technique also identified 71% more renal artery branches (p<0.001).

Fourteen of 66 breath held exams (21%) had blurring of the abdominal organs with the breath held technique compared to 108 of 120 exams (90%) during free breathing (p<0.001). The blurring of the abdominal organs indicate motion during the data acquisition. This occurred in 12 of 46 (26%), 58 second breath held exams, two of 12 (17%) 43 second exams, and none of the 29 second exams.

One patient had both a breath held exam as well as an exam performed during free breathing. In this patient, the renal artery anatomy was better defined on the breath-held exam.

All three breath held image times, 29, 43, and 58 seconds, had comparable arterial SNR* and CNR*. Axial, sagittal, and oblique reformations, however, had noticeably higher resolution with the 28 slice volume compared to the 12 slice volumes, presumably because of the smaller and more isotropic voxels.

Angiographic Correlation: Lateral aortograms were available to evaluate the celiac axis and proximal superior mesenteric artery in 8 of the 19 patients with angiographic correlation. Frontal and oblique aortograms were available in 18 patients with a total of 46 renal arteries. Two celiac stenoses, 1 celiac occlusion, 2 SMA stenoses, 3 renal artery stenoses and 1 renal artery occlusion were identified by MR and correctly graded. There were 3 discrepancies including a mild celiac stenosis graded as moderate by MR, a moderate renal artery stenosis graded as normal by MR and a normal renal artery graded as moderately stenotic by MR. In addition, in one patient with a liver transplant, thrombocytosis, and a history of Budd Chiari syndrome who had been on long term anticoagulation, MR graded the left renal artery as severely stenotic. At angiography, the left renal artery was found to be occluded but the fresh thrombus could easily be crossed with a wire and successful balloon angioplasty was performed. We felt that most likely the renal artery progressed from severe stenosis to occlusion between the MR and conventional arteriography due to withdrawal of anticoagulation in preparation for angiography. Overall, the 3D gadolinium MRA studies were in agreement with conventional angiography in 15 of these 19 (79%) patients.

Ten of eleven (91%) accessory renal arteries demonstrated at angiography were also demonstrated on MRA. The one error occurred in a patient who could not hold his breath for the entire 58 seconds. In one patient, angiography failed to recognize a tiny upper polar artery because of superposition of SMA branches. It was identified only in retrospect following analysis of the 3D gadolinium MRA.

Associated Lesions: Six patients had abdominal aortic aneurysms. Additional pulse sequences were required to image the anterior extent of the aneurysms and to evaluate mural thrombus. Renal or splanchnic artery reconstructions were imaged postoperatively in 6 patients including three with aortorenal bypass grafts. None of these studies were impaired by metallic clip artifacts. One of these patients exhibited a small renal infarct following a renal artery endarterectomy. A type III aortic dissection involving the abdominal aorta was seen in one case and confirmed by angiography. MRA demonstrated the dissection and correctly characterized the relationship of the true lumen to the celiac, superior mesenteric and renal artery origins. Enhancing renal masses were identified in two patients that were confirmed following nephrectomy to be renal cell carcinoma. However, the technique was not used to screen for renal masses because the posterior portions of the kidneys were excluded.

Adverse Reactions: All patients tolerated the procedure well. There were no allergic type reactions. No patient experienced nausea. One patient described a transient metallic taste immediately after a 42 ml infusion of gadodiamide. Periexamination serum creatinine levels were available in 15 patients. In these patients, the mean serum creatinine level was $1.8 \pm 2.4$ mg/dl on the day of or the day before the MRA exam and $1.8 \pm 2.6$ mg/dl the next day. No gadolinium contrast extravasations occurred in any of the patients despite many of the intravenous lines being located in hand or distal forearm veins.

Comments: In this EXAMPLE, respiratory motion was suppressed or eliminated by acquiring images in a single breath. The reduction in imaging time required for breath holding would normally be expected to diminish image quality. Data in this series of 63 patients, however, demonstrate that the elimination of respiratory motion and the faster gadolinium infusion resulted in an improvement in image quality.

These fast, breath-held 3D images improved in several ways upon the 3D gadolinium-enhanced techniques performed without breath holding. First, the aorta and renal arteries had higher SNR* and CNR*. Second, the distal renal arteries and renal artery branches were seen in a larger proportion of patients. Third, accessory renal arteries were correctly identified with greater frequency. Fourth, fewer patients had blurring of the abdominal organs. Fifth, visualization of differential enhancement between normal and ischemic kidneys allowed assessment of the hemodynamic significance of stenoses.

The imaging technique of this EXAMPLE provided satisfactory results notwithstanding the fact that circulation time of the contrast agent was estimated based upon clinical impression. An more accurate circulation time may be obtained by measuring the actual circulation time in advance of contrast agent injection by using decholin, saccharin, magnesium sulfate, or a test bolus of gadolinium.

The imaging technique of this Example, however, may be implemented in conjunction with the detection-imaging technique of the present invention which provides precise synchronization between collection of image data which is representative of the center of k-space and the arterial phase of contrast enhancement.

Another aspect of this Example included the patient's ability to breath hold. Many of the patients were able to hold their breath for 29, 43 or 58 seconds. In 14 patients, however, image "blurring" indicated that they either did not sustain the breath hold for the entire scan or they were moving their diaphragm despite breath holding. Most of the blurring occurred in the 58 second studies suggesting that the problem was sustaining the long breath hold.

The blurring may be alleviated or minimized with the use of faster scanners which acquire the necessary 3D volume in less time. It may also be improved or corrected by using a wider bandwidth. Increasing the bandwidth from 16 to 32 kHz reduces the 28 slice scan time from 58 to 43 seconds on our equipment. Such a change in the frequency or bandwidth may result in a decrease in SNR.

A 45 degree flip angle was used in this study, anticipating that errors in timing the infusion would result in a lower than expected arterial blood gadolinium concentration during the acquisition of the central portion of k-space. Should this timing be optimal, an improvement in the image contrast may be obtained by increasing the flip angle. When the arterial T1 is reduced to less than 50 msec, flip angles larger than 45 degrees will extract more signal from the arterial blood and, at the same time, achieve greater background suppression. In a preferred embodiment, a flip angle of about 60 degrees may be optimal when 42 ml of gadolinium is injected over 30 seconds, timed to perfectly coincide with the center of k-space.

Various preferred embodiments of the present invention have been described. It is understood, however, that changes, modifications and permutations can be made without departing from the true scope and spirit of the present invention as defined by the following claims, which are to be interpreted in view of the foregoing.

TABLE 1

Infusion Rates of Gadolinium Chelates at 24° C.

|  | Size | Gd-DTPA | Gadoteridol | Gadodiamide |
|---|---|---|---|---|
| Viscosity @ 20° C. [cP]* |  | 4.9 | 2.0 | 2.0 |
| Flow Restrictor |  | Infusion Rate |  |  |
| Needles |  |  |  |  |
| BD ® | 18 g 1.5" | 100 | 126 | 120 |
| Terumo ® | 20 g 1.5" | 44 | 66 | 64 |
| Terumo ® | 21 g 1.5" | 27 | 47 | 44 |
| Terumo ® | 22 g 1.5" | 15 | 29 | 23 |
| Terumo ® | 23 g 1" | <4 | <4 | <4 |
| Butterflies |  |  |  |  |
| ABBOTT ® | 21 g .75" | 21 | 37 | 36 |
| ABBOTT ® | 23 g .75" | 8 | 19 | 18 |
| ABBOTT ® | 25 g .375" | <4 | 8 | 7.3 |
| Orifice | 0.010" | 21 | 25 | 25 |

*Values provided by manufacturer (Nycomed)

TABLE 2

Aorta/IVC Signal Intensity Ratios for Dynamic 3D Imaging

| Patient # - sex | Age | Primary Indication | Heart Disease | Creatinine | Signal Intensity During Injection | | | |
|---|---|---|---|---|---|---|---|---|
|  |  |  |  |  | Aorta | IVC | ratio** | p value |
| 1-m | 83 | AAA | yes* | 2 | 7.9 ± 1.0 | 3.9 ± 0.6 | 2.0 | <.0001 |
| 2-f | 73 | hypertension | yes* | .8 | 11 ± 1.0 | 8.2 ± 1.3 | 1.4 | .0002 |
| 3-m | 73 | claudication | yes | 2.2 | 10 ± 2.0 | 3.7 ± 0.5 | 2.8 | .0003 |
| 4-f | 67 | hypertension | no | .9 | 10 ± 0.4 | 5.1 ± 0.6 | 2.0 | <.0001 |
| 5-f | 70 | hypertension | yes* | 3 | 8.9 ± 0.9 | 4.5 ± 0.4 | 2.0 | <.0001 |
| 6-m | 67 | renal failure | yes | 6 | 11 ± 0.5 | 4.9 ± 0.4 | 2.2 | <.0001 |
| 7-f | 80 | AAA | yes | 1.8 | 10 ± 0.4 | 5.9 ± 0.5 | 1.8 | <.0001 |
| 8-f | 76 | renal failure | yes* | 3.6 | 9.1 ± 0.6 | 5.0 ± 0.6 | 1.8 | <.0001 |
| 9-m | 68 | AAA | no | 1 | 11 ± 0.5 | 7.2 ± 0.3 | 1.4 | <.0001 |
| 10-m | 70 | claudication | yes | 1.2 | 11 ± 0.5 | 5.4 ± 0.3 | 2.0 | <.0001 |
| 11-m | 74 | hypertension | no | 1 | 8.9 ± 0.3 | 6.0 ± 0.8 | 1.5 | <.0001 |
| 12-m | 80 | hypertension | yes* | 3.2 | 10 ± 0.4 | 3.8 ± 0.9 | 2.6 | <.0001 |
| 13-m | 74 | AAA | yes | 4 | 9.8 ± 1.0 | 3.7 ± 0.8 | 2.6 | <.0001 |
| 14-f | 67 | AAA | no | 1 | 10 ± 0.3 | 5.9 ± 0.6 | 1.8 | <.0001 |
| 15-m | 67 | hypertension | no | 1.5 | 11 ± 0.9 | 4.6 ± 0.9 | 2.4 | <.0001 |
| 16-f | 71 | claudication | yes* | 6 | 11 ± 1.3 | 3.1 ± 0.6 | 3.5 | <.0001 |
|  |  | AVERAGE |  |  | 10 ± 0.9 | 5.1 ± 1.4 | 2.0 | <.0001 |

*cardiac disease with history of CHF
**Aorta/IVC signal intensity ratio

TABLE 3

Average Signal-To-Noise Ratios During and Post Gadopentetate Dimeglumine Injection

|  | Dynamic Injection | Post Injection | Ratio Dynamic/Post |
|---|---|---|---|
| ARTERIES |  |  |  |
| Aorta | 10 ± 0.9 | 10 ± 1.4 | 1.0 |
| Iliac Artery | 9.8 ± 1.3 | 10 ± 1.3 | .98 |
| Renal Artery | 9.7 ± 1.9 | 10 ± 2.5 | .99 |
| Celiac & SMA | 10 ± 1.7 | 11 ± 1.8 | .91 |
| VEINS |  |  |  |
| IVC | 5.1 ± 1.4 | 9.5 ± 1.3** | .54 |
| Iliac Vein | 4.7 ± 1.6* | 9.2 ± 1.3** | .51 |
| Renal Vein | 6.2 ± 1.8* | 9.1 ± 1.9** | .68 |
| Hepatic Vein | 7.5 ± 2.1* | 8.3 ± 1.0** | .90 |
| Portal Vein | 8.3 ± 1.6* | 9.0 ± 3.3** | .92 |
| BACKGROUND |  |  |  |
| Kidney | 7.3 ± 1.0 | 8.3 ± 1.0 | .88 |
| Liver | 5.3 ± 0.6 | 5.8 ± 1.8 | .91 |
| Spleen | 5.9 ± 2.3 | 6.3 ± 2.3 | 1.1 |
| Fat | 4.3 ± 0.7 | 4.0 ± 0.8 | 1.1 |
| Muscle | 2.4 ± 0.5 | 3.2 ± 0.7 | .75 |

*p > 0.01 compared to IVC signal intensity
**p > 0.01 compared to signal intensity for dynamic injection
***standard deviation of signal in the space outside the patient

TABLE 4

Effect of Cardiac Disease, Claudication and Aneurysms on Aorta/IVC Signal Intensity Ratio

| Subgroup | No. of Patients | Aorta/IVC* | p value |
|---|---|---|---|
| Cardiac Disease | 12 | 2.2 ± 0.6 | 0.08 |
| No Cardiac Disease | 4 | 1.8 ± 0.4 | 0.08 |
| Claudication | 4 | 2.6 ± 0.8 | 0.12 |
| No Claudication | 12 | 2.0 ± 0.4 | 0.12 |
| Aneurysm | 7 | 2.2 ± 0.7 | 0.32 |
| No Aneurysm | 9 | 2.0 ± 0.5 | 0.32 |

*Signal Intensity Ratio

TABLE 5

Effect of Injection Method on
Aorta Signal-to-Noise and Contrast-to-Noise Ratios

| Pulse Sequence | Contrast Injection Method | # of patients | Image time/cm (sec/cm) | Voxel Volume (mm³) | Saturation Artifacts | Pulsatility Artifacts | Aorta SNR | Aorta/IVC SI ratio | Aorta-IVC CNR | Aorta-fat CNR | Aorta-muscle CNR |
|---|---|---|---|---|---|---|---|---|---|---|---|
| 2D TOF | No gado | 11 | 40 | 6.0 | yes | yes | 8.2 ± 2.8 | 3.7 ± 1 | 5.8 ± 1.9 | 5.5 ± 2 | 6.8 ± 2.4 |
| MOTSA | No gado | 12 | 92 | 4.7 | yes | no | 8.9 ± 2.5 | 2.7 ± 0.9 | 5.1 ± 1.8 | 4.9 ± 1.7 | 6.3 ± 1.9 |
| Gado: 3D | non-dynamic | 16 | 9 | 3.1 | no | no | 9 ± 2.0 | 1.1 ± 0.1 | 0.6 ± 0.5 | 5.4 ± 1.5 | 6.2 ± 1.9 |
| Gado: 3D | bolus* | 12 | 9 | 3.1 | no | no | 12 ± 2.4 | 1.2 ± 0.2 | 2.7 ± 1.4 | 7.5 ± 1.6 | 9.1 ± 1.9 |
| Gado: 3D | infusion**[1] | 20 | 9 | 3.1 | no | no | 10 ± 1.2 | 2.0 ± 0.5 | 4.7 ± 1.4 | 5.4 ± 1.1 | 7.3 ± 1.1 |
| Gado: 3D | infusion**[2] | 20 | 5.5 | 3.1 | no | no | 10 ± 2 | 2.4 ± 0.8 | 5.6 ± 1.7 | 6.8 ± 1.9 | 8.2 ± 1.7 |

SNR = signal-to-noise ratio
CNR = contrast-to-noise ratio
*gadopentetate dimeglumine given dynamically as a bolus within the first 2 minutes of the acquisition.
**gadopentetate dimeglumine given dynamically as a constant infusion spread over the entire acquisition.
[1]5 minutes
[2]3 minutes

TABLE 6

Characteristics of Abdominal Aortic Aneurysms

| | |
|---|---|
| Suprarenal | 11 |
| Pararenal | 6 |
| Juxtarenal | 6 |
| Infrarenal | 20 |
| Mean Diameter (min–max) | 5.4 (3–8.7) cm |
| Thrombus | 35 (81%) |
| Inflammatory AAA | 1 (2%) |
| Leaking AAA | 1 (2%) |
| Retro-Aortic Renal Vein | 6 (14%) |
| Accessory Renal Arteries | 5 (12%) |

TABLE 7

Effect of Breath Holding on Coronal 3D Gadolinium-enhanced MRA

| | Free Breathing | Breath Holding | p-value |
|---|---|---|---|
| # of Patients in coronal plane | 104 | 48 | |
| # of Exams in coronal plane | 120 | 51 | |
| Imaging Time (minutes) | 3:26 | 0:29–0:58 | |
| Mean Contrast Dose (mMol/Kg) | 0.31 | 0.30 | |
| # of Kidneys in Which Renal Artery Branches Seen | 84/236 (36%) | 86/95 (91%) | <0.001 |
| Mean # of Renal Artery Branches Seen | 1.4 ± 0.7 | 2.4 ± 1.0 | <0.001 |
| SNR* | | | |
| Aorta | 9.5 ± 2.8 | 14 ± 4.6 | <0.001 |
| Proximal Renal Artery | 2.6 ± 1.6 | 3.3 ± 2.6 | 0.02 |
| Distal Renal Artery | 2.1 ± 2.5 | 3.1 ± 2.2 | 0.02 |
| CNR* | | | |
| Aorta | 7.0 ± 2.6 | 11 ± 4.1 | <0.001 |
| Proximal Renal Artery | 1.4 ± 1.3 | 2.3 ± 2.3 | 0.002 |
| Distal Renal Artery | 1.0 ± 1.6 | 2.2 ± 2.1 | <0.001 |

What is claimed is:

1. A magnetic resonance imaging system for imaging an artery of a patient using an administered magnetic resonance contrast agent, the magnetic resonance imaging system comprising:

a monitor unit to allow an operator to observe a change in the concentration of the contrast agent in a region of interest;

an operator interface to generate an image acquisition signal in response to an input from an operator wherein the operator generates the input after observing a change in the concentration of the contrast agent in the region of interest; and magnetic resonance imaging unit to collect image data of an imaging sequence to image the artery, wherein the magnetic resonance imaging unit, in response to the image acquisition signal, collects image data which is representative of the central portion of k-space near the beginning of the imaging sequence and a portion of the periphery of k-space thereafter.

2. The magnetic resonance imaging system of claim 1 wherein the magnetic resonance imaging unit generates a series of images and wherein the monitor unit receives the images and depicts the images as a temporal pattern of the arrival of the contrast agent in the region of interest.

3. The magnetic resonance imaging system of claim 1 wherein the magnetic resonance imaging unit continuously or periodically generates images of the region of interest and wherein the monitoring unit displays the images of the region of interest.

4. The magnetic resonance imaging system of claim 1 further including a magnetic resonance injection unit to inject the contrast agent into the patient before or while the magnetic resonance imaging unit continuously or periodically generates images of the region of interest that are displayed by the monitoring unit.

5. A method of imaging an artery of a patient using magnetic resonance imaging and an administered magnetic resonance contrast agent, the method comprising:

monitoring a region of interest to observe a change in the concentration of the contrast agent in a region of interest;

collecting image data of a magnetic resonance imaging sequence wherein the image data which is representative of the central portion of k-space is collected near the beginning of the imaging sequence and while the concentration of contrast agent in the artery is substantially greater than a concentration of contrast agent in veins adjacent to the artery.

6. The method of claim 5 wherein the imaging sequence is a 3D imaging sequence.

7. The method of claim 5 wherein monitoring the region of interest includes continuously or periodically monitoring the region of interest to detect the arrival of the contrast agent in the region of interest.

8. The method of claim 5 further including administering the magnetic resonance contrast agent to the patient as a bolus type injection.

9. The method of claim 8 wherein a substantial portion of the peripheral portion of k-space is collected after collecting the image data which is representative of the central portion of k-space.

10. The method of claim 8 further including instructing the patient to hold his breath before collecting image data which is representative of the central portion of k-space.

11. The method of claim 8 wherein monitoring the region of interest includes periodically measuring the response of the region of interest to magnetic resonance pulses.

12. The method of claim 8 wherein monitoring the region of interest includes visually displaying the region of interest to detect the onset of arterial phase of contrast enhancement in the artery.

13. The method of claim 8 wherein monitoring the region of interest includes visually displaying the region of interest to detect the arrival of the administered magnetic resonance contrast agent in the artery.

14. A method of imaging an artery of a patient using magnetic resonance imaging and an administered magnetic resonance contrast agent, the method comprising:

monitoring a region of interest by generating a series of images depicting the temporal pattern of the arrival of the contrast agent in the region of interest;

collecting image data of a magnetic resonance imaging sequence wherein the image data which is representative of the central portion of k-space is collected near the beginning of the sequence and while the concentration of contrast agent in the artery is substantially greater than a concentration of contrast agent in veins adjacent to the artery.

15. The method of claim 8 wherein the imaging sequence is a 3D imaging sequence.

16. The method of claim 15 wherein collecting image data of the magnetic resonance imaging sequence includes collecting the image data after visually detecting the arrival of the administered magnetic resonance contrast agent in the region of interest.

17. The method of claim 15 wherein a substantial portion of the image data which is representative of the peripheral portion of k-space is collected after collecting the image data which is representative of the central portion of k-space.

18. The method of claim 14 further including instructing the patient to hold his breath before collecting image data which is representative of the central portion of k-space.

19. The method of claim 14 wherein the central portion of the k-space is collected in response to detecting the arrival of the contrast agent in the region of interest.

20. The method of claim 14 wherein a substantial portion of the image data which is representative of the peripheral portion of k-space is collected after collecting the image data which is representative of the central portion of k-space.

* * * * *

UNITED STATES PATENT AND TRADEMARK OFFICE
CERTIFICATE OF CORRECTION

PATENT NO. : 6,741,881 B2
DATED : May 25, 2004
INVENTOR(S) : Prince

It is certified that error appears in the above-identified patent and that said Letters Patent is hereby corrected as shown below:

Column 52,
Line 5, delete "8" and substitute -- 14 --.

Signed and Sealed this

Twenty-sixth Day of October, 2004

JON W. DUDAS
*Director of the United States Patent and Trademark Office*